United States Patent
Tartz

(10) Patent No.: US 11,820,402 B2
(45) Date of Patent: Nov. 21, 2023

(54) MOTION SICKNESS DETECTION SYSTEM FOR AUTONOMOUS VEHICLES

(71) Applicant: QUALCOMM Incorporated, San Diego, CA (US)

(72) Inventor: Robert Tartz, San Marcos, CA (US)

(73) Assignee: QUALCOMM Incorporated, San Diego, CA (US)

(*) Notice: Subject to any disclaimer, the term of this patent is extended or adjusted under 35 U.S.C. 154(b) by 599 days.

(21) Appl. No.: 16/920,410

(22) Filed: Jul. 2, 2020

(65) Prior Publication Data

US 2022/0001893 A1    Jan. 6, 2022

(51) Int. Cl.
*A61B 3/113*   (2006.01)
*A61B 3/14*    (2006.01)
(Continued)

(52) U.S. Cl.
CPC ..... *B60W 60/0013* (2020.02); *A61B 5/02055* (2013.01); *A61B 5/165* (2013.01);
(Continued)

(58) Field of Classification Search
CPC ............. B60W 60/0013; B60W 40/08; B60W 2420/42; B60W 2540/22;
(Continued)

(56) References Cited

U.S. PATENT DOCUMENTS 10,559,307 B1   2/2020   Khaleghi
2015/0328985 A1*  11/2015  Kim ............... G08B 21/06
                                                180/272
(Continued)

FOREIGN PATENT DOCUMENTS

DE   102017208283   5/2018
DE   102018203898   9/2019
GB       2567856    5/2019

OTHER PUBLICATIONS

Cowings P.S., et al., "General Autonomic Components of Motion Sickness" NASA-CR-176516, N86-19886, California State College, 37 P HC A03/ MF A01, CSCL 06S, Unclas, G3/52 16271, Sep. 1986, 37 Pages.

(Continued)

*Primary Examiner* — Adam R Mott
*Assistant Examiner* — Heather J Keniry
(74) *Attorney, Agent, or Firm* — QUALCOMM Incorporated

(57) ABSTRACT

Techniques described herein include detecting a degree of motion sickness experienced by a user within a vehicle. A suitable combination of physiological data (heart rate, heart rate variability parameters, blood volume pulse, oxygen values, respiration values, galvanic skin response, skin conductance values, and the like), eye gaze data (e.g., images of the user), vehicle motion data (e.g., accelerometer, gyroscope data indicative of vehicle oscillations) may be utilized to identify the degree of motion sickness experienced by the user. One or more autonomous actions may be performed to prevent an escalation in the degree of motion sickness experienced by the user or to ameliorate the degree of motion sickness currently experienced by the user.

27 Claims, 12 Drawing Sheets

(51) Int. Cl.
| | |
|---|---|
| A61B 5/00 | (2006.01) |
| A61B 5/01 | (2006.01) |
| A61B 5/0205 | (2006.01) |
| A61B 5/024 | (2006.01) |
| A61B 5/0295 | (2006.01) |
| A61B 5/0533 | (2021.01) |
| A61B 5/16 | (2006.01) |
| A61M 21/00 | (2006.01) |
| B60W 30/02 | (2012.01) |
| B60W 40/08 | (2012.01) |
| B60W 50/00 | (2006.01) |
| B60W 50/14 | (2020.01) |
| B60W 60/00 | (2020.01) |
| G05D 1/00 | (2006.01) |
| G06F 3/01 | (2006.01) |
| G16H 40/67 | (2018.01) |
| G16H 50/30 | (2018.01) |
| G16H 50/50 | (2018.01) |
| G16H 50/70 | (2018.01) |

(52) U.S. Cl.
CPC .......... *A61B 5/6814* (2013.01); *A61B 5/6825* (2013.01); *A61B 5/7278* (2013.01); *A61B 5/7282* (2013.01); *B60W 40/08* (2013.01); *G05D 1/0088* (2013.01); *G16H 40/67* (2018.01); *G16H 50/30* (2018.01); *G16H 50/50* (2018.01); *G16H 50/70* (2018.01); *A61B 3/113* (2013.01); *A61B 3/14* (2013.01); *A61B 5/01* (2013.01); *A61B 5/024* (2013.01); *A61B 5/0295* (2013.01); *A61B 5/0533* (2013.01); *A61M 21/00* (2013.01); *A61M 2205/3303* (2013.01); *B60W 2420/42* (2013.01); *B60W 2540/22* (2013.01); *B60W 2540/221* (2020.02); *B60W 2540/225* (2020.02); *G05D 2201/0213* (2013.01); *G06F 3/013* (2013.01)

(58) Field of Classification Search
CPC ..... B60W 2540/221; B60W 2540/225; B60W 2420/905; B60W 2520/00; B60W 30/025; A61B 5/02055; A61B 5/165; A61B 5/6814; A61B 5/6825; A61B 5/7278; A61B 5/7282; A61B 3/113; A61B 3/14; A61B 5/01; A61B 5/024; A61B 5/0295; A61B 5/0533; G05D 1/0088; G05D 2201/0213; G16H 40/67; G16H 50/30; G16H 50/50; G16H 50/70; A61M 21/00; A61M 2205/3303; G06F 3/013
See application file for complete search history.

(56) References Cited

U.S. PATENT DOCUMENTS

| | | | | |
|---|---|---|---|---|
| 2016/0167672 | A1* | 6/2016 | Krueger | G16H 40/63 340/576 |
| 2017/0136842 | A1* | 5/2017 | Anderson | A61B 5/4023 |
| 2017/0291538 | A1* | 10/2017 | Sivak | A61M 21/02 |
| 2018/0370461 | A1* | 12/2018 | Solar | A61M 21/00 |
| 2019/0022347 | A1* | 1/2019 | Wan | A61B 5/18 |
| 2019/0073547 | A1* | 3/2019 | el Kaliouby | G06N 3/084 |
| 2019/0133511 | A1* | 5/2019 | Migneco | A61B 5/0077 |
| 2019/0357834 | A1 | 11/2019 | Aarts et al. | |
| 2020/0114150 | A1* | 4/2020 | Monteiro | A61N 1/36025 |
| 2020/0353934 | A1* | 11/2020 | Vulcu | A61B 5/165 |
| 2021/0031789 | A1* | 2/2021 | Moriura | B60H 3/0007 |
| 2022/0047196 | A1* | 2/2022 | Kuboi | G06T 7/20 |

OTHER PUBLICATIONS

Dahlman J., "Psychophysiological and Performance Aspects on Motion Sickness", Linkoping University Medical Dissertations No. 1071, 2009, 72 Pages.

Diels C., et al., "User Interface Considerations to Prevent Self-Driving Carsickness", Adjunct Proceedings of the 7th International Conference on Automotive User Interfaces and Interactive Vehicular Applications, Sep. 2015, pp. 14-19.

Diels C., "Will Autonomous Vehicles Make Us Sick?", Contemporary Ergonomics and Human Factors, Boca Raton, FL, CRC Press, Oct. 2014, pp. 301-307.

Gavgani A.M., et al., "Profiling Subjective Symptoms and Autonomic Changes Associated With Cybersickness", Published in Autonomic Neuroscience: Basic and Clinical vol. 203, Issue Mar. 2017, pp. 1-21.

Gianaros P.J., et al., "A Questionnaire for the Assessment of the Multiple Dimensions of Motion Sickness", NIH Public Access, Aviat Space Environ Medicine, 72(2), Feb. 2001, pp. 1-10.

Golding J.F., et al., "Phasic Skin Conductance Activity and Motion Sickness", Aviation, Space & Environmental Medicine, vol. 63, No. 3, Mar. 1992, pp. 165-171.

Griffin M.J., et al., "An Experimental Study of Low-Frequency Motion in Cars", Proceedings of the Institution of Mechanical Engineers Part D Journal of Automobile Engineering, vol. 218, Issue 11, Nov. 1, 2004, pp. 1231-1238.

Lacount L.T., et al., "Static and Dynamic Autonomic Response with Increasing Nausea Perception", NIH Public Access, Aviat Space Environ Medicine, 82(4), Apr. 2011, pp. 1-20.

Nalivaiko E., et al., "Motion Sickness, Nausea and Thermoregulation: The "Toxic" Hypothesis", Temperature, vol. 1, Issue 3, Oct. 2014, pp. 164-171.

Nobel G., et al., "Effects of Motion Sickness on Thermoregulatory Responses in a Thermoneutral Air Environment", European Journal of Applied Physiology, 112(5), May 2012, pp. 1717-1723.

Sivak M., et al., "Motion Sickness in Self-Driving Vehicles", University of Michigan Transportation Research Institute, UMTRI-2015-12, Apr. 2015, 15 Pages.

Sjors A., et al., "Effects of Motion Sickness on Encoding and Retrieval Performance and on Psychophysiological Responses", Journal of Ergonomics, vol. 4, Issue 1, Jan. 2014, 8 Pages.

Turner M., et al., "Motion Sickness in Public Road Transport: The Effect of Driver, Route and Vehicle", Ergonomics, vol. 42, No. 12, Dec. 1999, pp. 1646-1664.

International Search Report and Written Opinion—PCT/US2021/029635—ISA/EPO—dated Jul. 16, 2021.

* cited by examiner

| Sick | Stress | Gaze | Oscillate | Classification |
|---|---|---|---|---|
| 0 | 0 | 0 | 0 | None |
| 0 | 0 | 0 | 1 | Low |
| 0 | 0 | 1 | 0 | Low |
| 0 | 0 | 1 | 1 | Moderately Low |
| 0 | 1 | 0 | 0 | Moderately Low |
| 0 | 1 | 0 | 1 | Moderately High |
| 0 | 1 | 1 | 0 | Moderately High |
| 0 | 1 | 1 | 1 | High |
| 1 | X | X | X | Very High |

MOTION SICKNESS DETECTION SYSTEM FOR AUTONOMOUS VEHICLES

BACKGROUND

Technologies related to autonomous or partially autonomous vehicles have been advancing over the years. Motion sickness is predicted to occur more frequently in autonomous vehicles due to the shift in role from driver to passenger as the passenger can engage in activities that increase their susceptibility to motion sickness (e.g., reading, texting, device use, etc.). Motion sickness not only results in nausea and physiological discomfort, but can also affect cognitive and emotional state (e.g., anxiety, lack of concentration). It may be beneficial to ascertain the degree of motion sickness a person may be experiencing. Early detection may be useful in order to activate various strategies to prevent and/or mitigate symptoms.

BRIEF SUMMARY

Techniques described herein provide for detecting a degree of motion sickness currently being experienced by a person in a vehicle. Depending on the degree of motion sickness detected, a number of remedial actions and/or preventative strategies may be employed.

Some embodiments may include a method for detecting motion sickness in a person within a vehicle. The method may include obtaining, by one or more processors, first physiological data from a plurality of sensor devices. The method may further include, obtaining, by the one or more processors, vehicle motion data indicating a frequency of oscillations of the vehicle. The method may further include calculating, by the one or more processors, a motion sickness score based at least in part on the first physiological data and the vehicle motion data, the motion sickness score indicating a likelihood that the person is experiencing motion sickness. The method may further include detecting, by the one or more processors, that the person is experiencing motion sickness based at least in part on the motion sickness score.

Some embodiments may include a computing device. The computing device may comprise a memory storing executable instructions for preventing or ameliorating a degree of motion sickness experienced by a user within a vehicle and one or more processors communicatively coupled with the memory. In some embodiments, the one or more processors are configured to execute the instructions to cause the computing device to perform operations. The operations may comprise obtaining physiological data from a plurality of sensor devices. The operations may comprise obtaining vehicle motion data indicating a frequency of oscillations of the vehicle. The operations may comprise calculating a motion sickness score based at least in part on the physiological data and the vehicle motion data. The operations may comprise detecting that the user is experiencing a degree of motion sickness based at least in part on the motion sickness score. The operations may comprise causing performance of an autonomous vehicle action in response to determining that the user is experiencing the degree of motion sickness. In some embodiments, causing the autonomous vehicle action to be performed ameliorates the degree of motion sickness experienced by the user and/or prevents an escalation in the degree of motion sickness experienced by the user at the subsequent time.

Some embodiments may comprise a non-transitory computer-readable medium. The non-transitory computer-readable medium may comprise stored instructions for preventing or ameliorating a degree of motion sickness experienced by a user within a vehicle. In some embodiments, the instructions, when executed by one or more processing units, cause the one or more processing units to perform operations. The operations may comprise obtaining physiological data from a plurality of sensor devices. The operations may comprise obtaining vehicle motion data indicating a frequency of oscillations of the vehicle. The operations may comprise calculating a motion sickness score based at least in part on the physiological data and the vehicle motion data. The operations may comprise detecting that the user is experiencing a degree of motion sickness based at least in part on the motion sickness score. The operations may comprise causing performance of an autonomous vehicle action in response to determining that the user is experiencing the degree of motion sickness. In some embodiments, causing the autonomous vehicle action to be performed ameliorates the degree of motion sickness experienced by the user and/or prevents an escalation in the degree of motion sickness experienced by the user at the subsequent time.

BRIEF DESCRIPTION OF THE DRAWINGS

FIG. 3 is a table illustrating various parameter value combinations for classifying a degree of motion sickness of a user of a vehicle, according to an embodiment.

Figure 1:
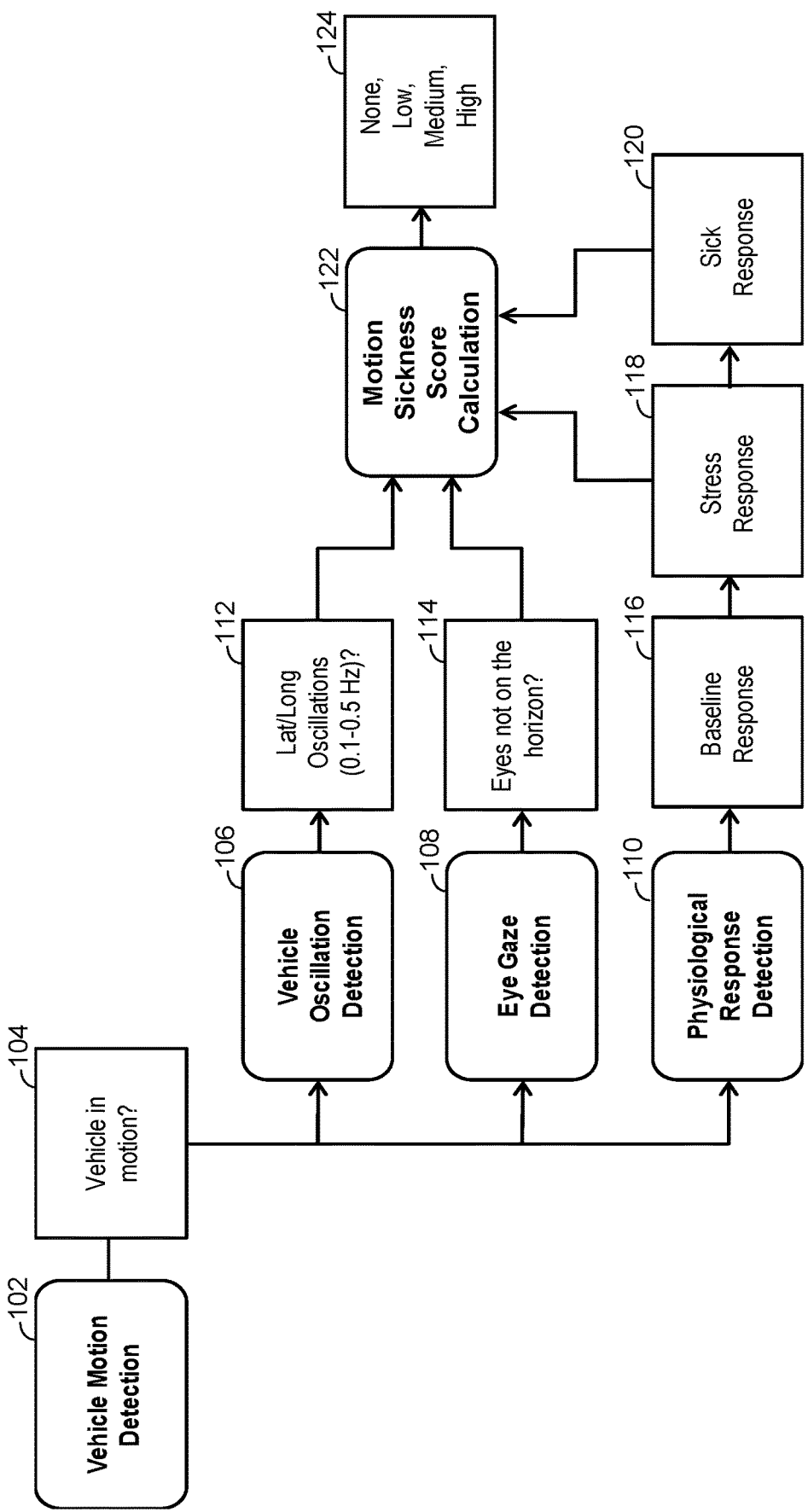
FIG. 1 is a simplified block diagram that illustrates a method for classifying a degree of motion sickness currently being experienced by a user in a vehicle, according to an embodiment.

Like reference symbols in the various drawings indicate like elements, in accordance with certain example implementations. In addition, multiple instances of an element may be indicated by following a first number for the element with a letter or a hyphen and a second number. For example, multiple instances of an element 110 may be indicated as 110-1, 110-2, 110-3 etc. or as 110a, 110b, 110c, etc. When referring to such an element using only the first number, any instance of the element is to be understood (e.g., element 110 in the previous example would refer to elements 110-1, 110-2, and 110-3 or to elements 110a, 110b, and 110c).

DETAILED DESCRIPTION

Several illustrative embodiments will now be described with respect to the accompanying drawings, which form a part hereof. While particular embodiments, in which one or more aspects of the disclosure may be implemented, are described below, other embodiments may be used and various modifications may be made without departing from the scope of the disclosure or the spirit of the appended claims.

It is estimated that 37% of American riders of autonomous vehicles are expected to experience motion sickness resulting at least in part from engaging in various activities such as reading, texting, and utilizing a smart phone or other device while the vehicle is in motion. Motion sickness susceptibility may be heightened when riding in autonomous vehicles because a person is incapable of controlling and/or anticipating the direction of motion and due to the conflict between the vestibular, proprioceptive, and visual senses (i.e., the perception of body movement as determined by the vestibular system of the inner ear versus the perception of body movement as perceived through sight and/or the perception of body movement as perceived by joints and/or muscles of the body). Motion sickness not only results in nausea and physiological discomfort, but can also affect cognitive and emotional state (e.g., anxiety, lack of concentration). Other symptoms may include stomach awareness/ discomfort, dizziness, lightheadedness, disorientation, sweating, clamminess, hot/cold flashes, drowsiness, irritability, uneasiness, and the like. Thus, it may be critical for safety to be able to ascertain a degree of motion sickness experienced by the driver, especially before transferring control of the vehicle to the driver after an autonomous driving session.

The experience of nausea occurs toward the end state of extreme motion sickness. But physiological data in conjunction with other vehicle data may signal the preliminary stages of motion sickness before nausea and/or other symptoms ensue. Early detection may enable various strategies to be activated to prevent and/or mitigate symptoms. Such strategies may include, but are not limited to, adjusting driving dynamics (e.g., speed, handling, acceleration, etc.), adjusting the sensory environment (e.g., adjusting lighting, playing music, providing alerts, adjusting sound volume, adjusting temperature settings, and/or air flow, modifying the olfactory environment such as providing a scent, etc.), adjusting a view of the horizon (e.g., adjusting a video display, increasing the viewing area of a window, etc.), and the like.

Embodiments provided herein utilize a combination of physiological data (heart rate, heart rate variability, blood volume pulse (e.g., amplitude), skin conductance/galvanic skin responses, skin temperature, etc.) and vehicle motion data (e.g., any suitable data identifying motion of the vehicle including amplitude and frequency of the oscillations of the vehicle and/or parts of the vehicle) to assess whether a person in the vehicle is experiencing motion sickness and/or a degree of motion sickness experienced by that person. As used herein, physiological data may include any suitable data associated with any suitable physiological attribute of a person (e.g., skin temperature, heart rate, heart rate variability, respiration rate, breath volume, blood oxygen level ($SpO_2$), skin conductance level (SCL) and skin conductance response (SCR) as measured from a skin conductance sensor (e.g., a galvanic skin response (GSR) sensor) galvanic skin response (GSR), electrodermal activity (EDA), electrodermal response (EDR), sympathetic skin response (SSR), peripheral autonomic surface potential, psychogalvanic reflex (PGR), sympathetic skin response (SSR), and the like).

In some embodiments, vehicle motion data may be captured by any suitable combination of accelerometers and/or gyroscopes of the vehicle. Low-frequency oscillations of 0.1-0.5 Hz in the lateral (front to back) or longitudinal (side to side) directions are the most likely of oscillations to contribute to motion sickness. Frequencies in this range are typically created by driver behavior: turning, braking, acceleration (not road conditions nor car construction).

In some embodiments, one or more cameras may be utilized to capture one or more images and/or videos (also referred to as "eye gaze data") of one or more passengers of the vehicle (e.g., the face of the passenger(s)). Utilizing any suitable image recognition techniques and/or eye tracking techniques, the gaze of the passenger may be identified (e.g., is the passenger looking out a window, does he have his eyes on the horizon, is he looking downward, reading, playing with his phone, etc.) It is best to have as large a field of view of the horizon as possible to minimize sickness symptoms. A constricted visual field results in increased sickness, since motion felt by the vestibular system would be greater than the motion seen by the visual system, leading to a conflict. The identification of the passenger's gaze can be utilized (e.g., in conjunction with the physiological data and/or the vehicle motion data) to determine a motion sickness score that indicates a degree of motion sickness likely being experienced by the passenger in real time.

There is a sequence of physiological responses that occur prior to the person feeling nauseous. In some embodiments, this sequence may be defined by a baseline response (e.g., indicating typical physiological data of the person), followed by a stress response (in which certain physiological responses are seen), before a sick response including nausea is experienced by the person. Vehicle data, physiological data, and eye gaze data may be collected over time. In some embodiments, observing this sequence based on the data collected over time may increase the likelihood (e.g., a motion sickness score) that the person is experiencing motion sickness. Whereas, if the data collected over time does not indicate a stress response first, it may be determined that it is less likely the user is experiencing a sick response (e.g., nausea) currently.

Utilizing the disclosed techniques may enable motion sickness to be more accurately detected and/or detected earlier than conventional techniques. By detecting motion sickness more accurately and/or earlier, the techniques described herein can enable a safer autonomous driving experience as autonomous driving systems can be configured to retain control of the vehicle while the driver is experiencing motion sickness. In some embodiments, having knowledge of the fact a passenger of the vehicle is experiencing motion sickness can cause the autonomous driving system to perform one or more actions aimed at preventing and/or ameliorating the effects of motion sickness. For example, the autonomous driving system can reduce speed, take less aggressive and/or fewer turns. In some embodiments, the described techniques can be applied in other contexts. By way of example, similar techniques may be utilized to assess cybersickness (e.g., nausea) commonly experienced in virtual reality environments, augmented reality (AR) environments, and mixed reality (MR) environments.

FIG. 1 is a simplified block diagram that illustrates a method 100 for classifying a degree of motion sickness currently being experienced by a user in a vehicle, according to an embodiment. Means for performing the method 100 may include one or more hardware and/or software components of a vehicle, such as those illustrated in FIG. 8-10, which is described below.

Method 100 may begin at block 102, where operations for detecting vehicle motion is executed. In some embodiments, these operations may include collecting various sensor data from one or more accelerometers, gyroscopes, or other suitable inertial sensors. The vehicle motion data collected from these sensors may be analyzed to determine whether the vehicle is in motion.

The method may proceed to block 104 where a determination may be made using the vehicle motion data collected at block 102 as to whether the vehicle is in motion. In some embodiments, if the vehicle is determined to be stationary (e.g., not in motion), the method 100 may conclude. Alternatively, if the vehicle is determined to be in motion, the method 100 may proceed to block 106, block 108, and/or block 110. The operations of blocks 106, 108, and/or 110 may be executed in any suitable sequence or the operations of blocks 106, 108, and/or 110 may be executed substantially concurrently.

At block 106, a vehicle oscillation detection operation may be executed. As part of this operation, latitude (e.g., front to back) or longitude (side to side) oscillations (e.g., vibrations) of the vehicle may be identified. In some embodiments, one or more accelerometers, gyroscopes, and/or inertial sensors may be utilized to identify oscillations of the vehicle. By way of example, a 3-axis accelerometer may collect and identify data indicating an oscillation frequency of the vehicle. In some embodiments, the vehicle oscillation data may be collected as part of the vehicle motion detection operation conducted at block 102. Vehicle oscillation data may be collected by one or more sensors integrated into either the vehicle, or by one or more wearable devices, or any suitable combination of the above.

Once oscillation data has been collected, the method may proceed to block 112. At block 112, operations may be performed to determine whether the latitude and/or longitude oscillations fall within a predefined threshold range. By way of example, the threshold range may be defined as 0.1-0.5 Hz. In some embodiments, this range may be modified over time as motion sickness is observed and/or confirmed in the vehicle's passengers. Further details of threshold range modifications will be discussed below.

At block 108, eye gaze detection operations may be executed. In some embodiments, these operations may include obtaining one or more images and/or videos (referred to as "eye gaze data") of the user (or users) of the vehicle. The eye gaze data may include images of a face and/or eye region of the user. If there are multiple users of the vehicle, the eye gaze data may include features of some combination of those users. Any reference herein to an operation being performed with respect to one user can be understood to be similarly applicable in use cases in which multiple users are present.

Once eye gaze data has been collected at block 108, the method 100 may proceed to block 114. At block 114, operations may be performed to determine whether the user's gaze is on the horizon. In some examples, a user's gaze can be determined using a wearable device (e.g., AR glasses, non-display glasses, etc.). For example, an AR device may include an eye-tracking camera and/or an external camera from which the user's gaze can be identified. In some embodiments, an inertial measurement unit of the wearable device can be utilized to determine the gaze of the user. As yet another example, a camera faced toward the user may be utilized to identify the user's gaze. For example, a camera may be attached to the dashboard of a vehicle, to the ceiling of a vehicle, to the windshield, or any suitable location from which the camera can be directed inward toward the user(s). Based on a known placement of the camera, the direction of the user's gaze may be determined. By way of example, if the camera is known to be placed at a windshield, then it may be determined that the user is looking out the windshield if the user's eyes are fully visible (or some threshold amount of the eyes are visible) in the image captured by the camera. An image recognition technique may be employed to identify whether the user's eyes are fully visible (indicating the user is looking in a direction of the camera, although not necessary directly at the camera). Similarly, the user's gaze could be determined to be directed to various directions by analyzing the features of the user's head or face which are visible within the image/video and/or the features that are not. Any suitable eye tracking techniques may be similarly employed to identify the direction of the user's gaze.

At block 110, physiological response detection operations may be executed. In some embodiments, these operations may include collecting physiological data from one or more physiological sensors of the vehicle and/or from one or more wearable devices. As discussed above, physiological data may include any suitable data associated with any suitable physiological attribute of a person (e.g., skin temperature, heart rate, heart rate variability, respiration rate, breath volume, blood oxygen level ($SpO_2$), skin conductance level (SCL) and skin conductance response (SCR) as measured from a skin conductance sensor (e.g., a galvanic skin response (GSR) sensor) galvanic skin response (GSR), electrodermal activity (EDA), electrodermal response (EDR), sympathetic skin response (SSR), peripheral autonomic surface potential, psychogalvanic reflex (PGR), sympathetic skin response (SSR), and the like) captured by one or more corresponding physiological sensors.

Figure 2:
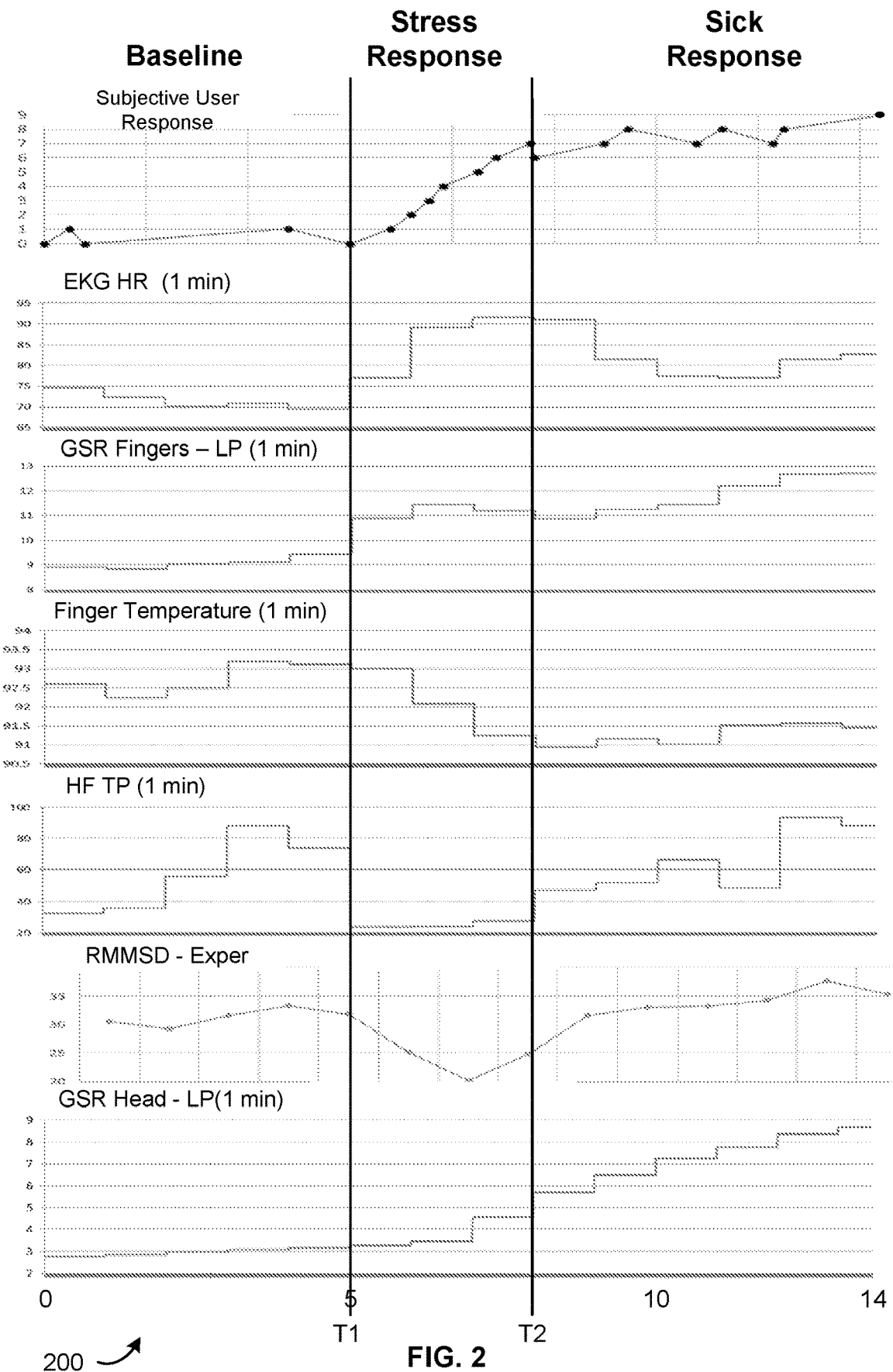
FIG. 2 is a collections of graphs that illustrates an example sequence of physiological parameters of the user indicating a progression from a baseline state, to experiencing a stress response, to experiencing a sick response (e.g., motion sickness), according to an embodiment.

FIG. 2 is a collections of graphs that illustrates an example sequence of physiological parameters of the user indicating a progression from a baseline state, to experiencing a stress response, to experiencing a sick response (e.g., a degree of motion sickness), according to an embodiment. In some embodiments, physiological parameters may be collected for some period of time (e.g., 5 minutes, 1 minute, 30 seconds, etc.) before the vehicle is in motion or at any suitable time the vehicle is stationary. In the example depicted in FIG. 2, a set of physiological sensors used to capture physiological data may include an EKG sensor (e.g., an electrocardiogram sensor, also referred to as an "ECG" sensor), a GSR sensor at the users fingers, a thermometer configured to measure skin temperature at the user's fingers, and a GSR sensor positioned at the user's forehead. The graphs corresponding to high frequency (HF) and root mean square of successive differences (RMSSD)) may be derived from the EKG data that has been captured over time. In some embodiments, physiological data (e.g., a set of physiological parameters such as heart rate, skin conductance, temperature, and the like) may be collected during a period of time (e.g., 1 minute, 5 minutes, 30 seconds) after motion has first commenced. In some embodiments, a wearable PPG sensor could be used to collect measurements (e.g., blood volume pulse) and physiological parameters (e.g., heart rate, heart rate variability, etc.) may be derived from the measurements. In the scenarios above, the collected physiological parameters may be stored locally and labeled as (e.g., associated) the user's baseline physiological parameters.

The graphs 200 of FIG. 2 collectively depict a stress response starting at T1. In some embodiments, the beginning symptoms of a stress response may include increased heart rate and a rise of galvanic skin response at the user's fingers. Approximately one minute later (e.g., give or take 10-15 seconds) temperature captured at the user's fingers may drop. In some embodiments, the stress response may include parasympathetic nervous system withdrawal as indicated by heart rate variability/low frequency, or heart rate variability/root mean square of successive differences as depicted in FIG. 2.

The user may be identified as experiencing motion sickness at T2 when the symptoms of the stress response are followed by symptoms of the sick response as depicted in FIG. 2. The sick response can include any suitable combination of: increased galvanic skin responses at the forehead and/or fingers, slightly increasing heart rate, stable or slightly increasing finger temperature and blood volume pulse amplitude, and/or stable or increasing HF/RMSSD.

Returning to FIG. 1, as physiological data is collected at block 110, the method 100 may proceed to block 116 where a baseline response may be identified for the user. In some embodiments, the physiological data may be collected near a time when the vehicle's motion began. Thus, this physiological data (e.g., physiological data corresponding to a 2-minute average when the vehicle was stationary, the first 5 minutes of motion, the 10 minutes of motion, 1 minute before motion commenced, 5 minutes before motion commenced, etc.) may be utilized to define a baseline response for the user. In some embodiments, a first set of physiological data parameters may be stored in local memory and associated with the user's baseline response.

Over time, more physiological data may be collected and the method 100 may proceed to block 118 where the system may determine whether the user is experiencing a stress response. As discussed above in connection with FIG. 2, determining that the user is experiencing a stress response may include determining the user's baseline response first and then identifying that a set of conditions are met. That is, a stress response may be defined as the occurrence of a base line response followed by a predefined set of changes in corresponding physiological parameters from the baseline response over a predefined threshold amount.

Even more physiological data may be collected and the method 100 may proceed to block 120 where the system may determine whether the user is experiencing a sick response. As discussed above in connection with FIG. 2, determining that the user is experiencing a sick response may include determining the user's baseline response first and then identifying that a set of conditions associated with a stress response are met, followed by a determination that another set of conditions associated with a sick response is met.

The method 100 may proceed to block 122, where operations for calculating a motion sickness score are executed. In some embodiments, the motion sickness score indicates a probability and/or a degree to which the user is experiencing motion sickness. The motion sickness score may be calculated based at least in part on the determinations made at blocks 112, 114, 116, 118, and 120 or any combination of those determinations. In some embodiments, a greater number of positive indications obtained from blocks 112, 114, 116, 118, 120, may produce a higher motion sickness score than would be the case for a fewer number of positive indications from blocks 112, 114, 116, 118, and 120. In some embodiments, the motion sickness score may be a numerical value that may be mapped to a classification (e.g., none, low, medium, and high). In other embodiments, the motion sickness score may be a classification rather than a numerical value.

FIG. 3 is a table 300 illustrating various parameter value combinations for classifying a degree of motion sickness of a person in a vehicle, according to an embodiment.

The column labeled "Sick" is intended to correspond to the determination made at block 120 of FIG. 1. A value of "0" in the Sick column indicates the determination at block 120 was that the user is not experiencing a sick response, while a value of "1" indicates that the determination at block 120 was that the user is experiencing a sick response.

The column labeled "Stress" is intended to correspond to the determination made at block 118 of FIG. 1. A value of "0" in the Stress column indicates the determination at block 118 was that the user is not experiencing a stress response, while a value of "1" indicates that the determination at block 118 was that the user is experiencing a stress response.

The column labeled "Gaze" is intended to correspond to the determination made at block 114 of FIG. 1. A value of "0" in the Gaze column indicates the determination at block 114 was that the user was not looking in the direction of the horizon, while a value of "1" indicates that the determination at block 118 was that the user was looking in the direction of the horizon.

The column labeled "Oscillate" is intended to correspond to the determination made at block 112 of FIG. 1. A value of "0" in the Oscillate column indicates the determination at block 112 was that the oscillations of the vehicle were determined be outside the predetermined range, while a value of "1" indicates that the determination at block 112 was that the oscillations of the vehicle were determined to fall in the predetermined range.

The column labeled "Classification" depicts the classification that may be assigned to data corresponding to each row of the table 300.

Returning to FIG. 1, in some embodiments, the operations performed at block 122 may include comparing the determinations obtained at blocks 112, 114, 118, and 120 to the table 300 of FIG. 3 that may be stored in local memory. Based at least in part on this comparison, a classification can be identified from the table and the user may be identified as experiencing no motion sickness, a low degree of motion sickness, a medium degree of motion sickness, or a high degree of motion sickness.

In some embodiments, a machine learning model (also referred to as a classification model) may be trained using supervised learning techniques and a training data set to classify new input data (e.g., physiological data, eye gaze data, vehicle motion data, or the like) as being indicative of the user experiencing some degree of motion sickness. In some embodiments, the training data set may include any suitable number of examples including any suitable combination of physiological data, eye gaze data, vehicle motion data, for which a classification (e.g., a degree of motion sickness experienced by the user) is known. The training data set may include any suitable number of examples that are indicative of a degree of motion sickness. Although the examples described herein utilize four classification values (e.g., none, stress, sick, low, medium, high), any suitable number of classifications may be similarly utilized. Example supervised learning algorithms may include regression algorithms (e.g., linear regression, logistic regression, etc.), decision trees, random forest, neural networks, naive Bayes, k-nearest neighbor, and the like. As a non-limiting example, a regression algorithm may be utilized to generate a mathematical model (e.g., the classification model) that models the relationship between two variables by fitting a linear equation to observed data (e.g., the training data set). Once the model is generated, new data (e.g., physiological data, eye gaze data, vehicle motion data) may be provided to the model, and in response, the model may provide a classification for the new data.

In some embodiments, the machine learning model may be improved over time to provide more accurate classifications. By way of example, new data may be provided to the model and a classification may be determined by the model. In some embodiments, feedback may be elicited from the user to confirm whether the classification was accurate. A user interface may be provided (e.g., via a touch screen of the vehicle) that enables the user to provide such feedback. If the feedback was accurate (or if the feedback was not accurate), the collected data may be labeled as such and added to the training data set. The model may be retrained and/or incrementally updated based at least in part on the training data set that now includes the new example(s).

As yet another example, a predefined rule set or a machine learning model may be utilized to calculate (or obtain) a numerical value corresponding to a motion sickness score. The motion sickness score can quantify a likelihood that the user is experiencing and/or a degree of motion sickness experienced by a user.

Figure 4C:
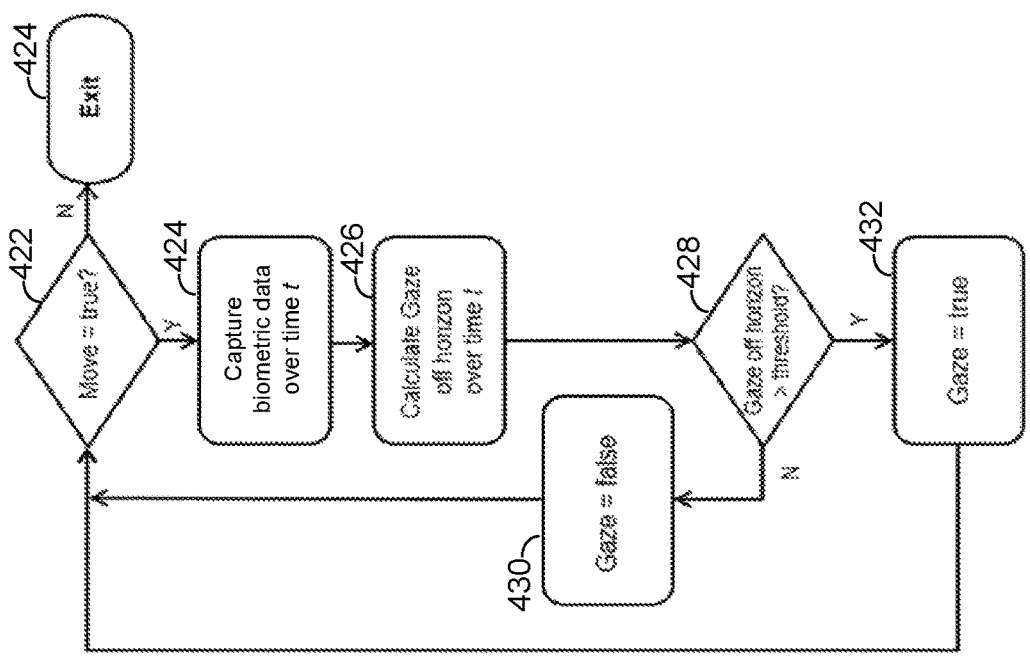
FIGS. 4A-4C are flowcharts that illustrate methods for determining a number of variable values, according to some embodiments.
Figure 4B:
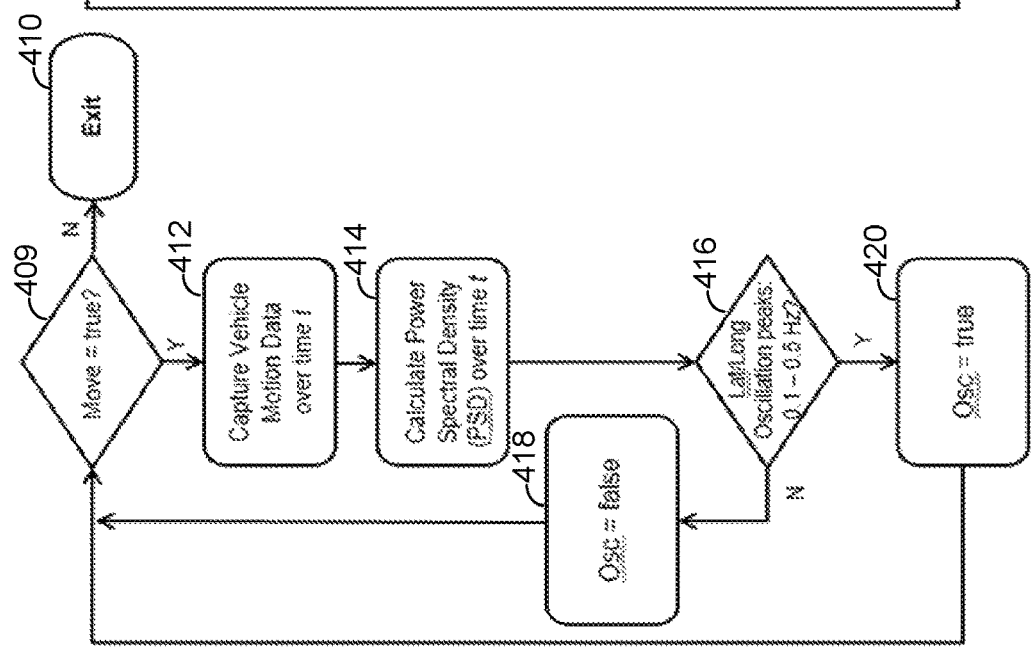
Figure 4A:
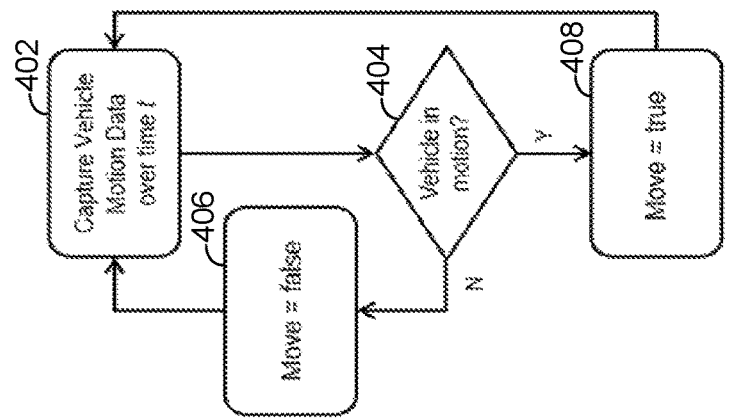

FIGS. 4A-4C are flowcharts that illustrate methods 400A-400C for determining a number of variable values, according to some embodiments. Means for performing the methods 400A, 400B, and/or 400C may include one or more hardware and/or software components of a vehicle, such as those illustrated in FIG. 8-10, which is described below. Prior to the execution of methods 400A-400C, various variables that maintain the determinations corresponding to blocks 104, 112, 114, 116, 118, and 120 may be initialized to a default value (e.g., false, indicating the condition corresponding to respective blocks has not been met).

FIG. 4A is a flowchart that illustrates method 400A, a method for determining whether a vehicle is in motion. The method 400A may begin at 402, where vehicle motion data may be captured over time t. Vehicle motion data may be collected by any suitable sensors (e.g., one or more of the vehicle sensor(s) 810 discussed below in connection with FIG. 8) including accelerometers, gyroscopes, magnetometers, and the like. In some embodiments, the vehicle motion data can be collected by one or more wearable devices such as a smart watch, glasses, an inertial measurement unit (IMU) of the vehicle, and the like. The vehicle motion data may be collected according to any suitable periodicity/ frequency, according to a predefined schedule, and/or according to any suitable predefined conditions.

At 404, a determination may be made from analyzing the vehicle motion data as to whether the vehicle is in motion. If the vehicle is not in motion, a variable (e.g., a "move" variable) may be set at 406 and the method 400A may return to 402 where additional vehicle motion data may be captured. This loop may continue any suitable number of times over time t. In some embodiments, time t may correspond to a total time during which the vehicle is in use (e.g., including times during which the vehicle is idling and stationary or in motion).

If the vehicle is determined to be in motion at 404, then the method 400A may proceed to 406, where a variable (e.g., a "move" variable) may be updated to indicate that the vehicle is in motion. Thereafter, the method 400A may return to 402 and the steps 402-408 may be repeated any suitable number of times over time t.

FIG. 4B is a flowchart that illustrates method 400B, a method for determining whether a vehicle is producing oscillations that fall in a predefined threshold (e.g., oscillation frequencies that may be determined to be more likely to elicit a stress and/or sick response in a user than other oscillation frequencies). The method 400B may begin at 409, where the "move" variable set at 406 may be checked. If the value of the variable indicates the vehicle is not in motion, method 400B may exit at 410. Alternatively, if the value of the move variable indicates the vehicle is in motion, the method 400B may proceed to 412.

At 412, vehicle motion data may be captured over time. This vehicle motion data may be of a similar type as that captured at 402 of method 400A but at a subsequent time. Once this additional vehicle motion data is captured, method 400B may proceed to 414 where a power spectral density (PSD) of the vehicle's vibrations may be calculated over time t using the additional vehicle motion data captured at 412. The power spectral density of the vehicle's vibration is the energy variation that takes place within the vehicle motion data (e.g., accelerometer readings), measured as frequency per unit of mass. In some embodiments, the energy variation may be decomposed along two perpendicular axes. A lateral component may indicate the amount of the energy variation of vibration that corresponds to an axis running from the front to the back of the car, while a longitude component may indicate the amount of the energy variation of vibration that corresponds to an axis running from one side to the opposing side of the vehicle.

At 416, a determination may be made as to whether any of the lateral or longitude components calculated at 414 fall within a predefined frequency range. As an example, the predefined frequency range may be 0.1 to 0.5 Hz. If the components of the vehicles oscillations do not fall within the predefined frequency range, the method 400B may proceed to 418 where a variable (e.g., an oscillation variable) may be set to a value indicating the same and the method 400B may proceed back to 408. This loop may continue any suitable number of times over time t so long as the oscillation components of the vehicle's vibration fail to fall within the predefined frequency range. In some embodiments, time t may correspond to a total time during which the vehicle is in use (e.g., including times during which the vehicle is idling and stationary or in motion).

Alternatively, if the components of the vehicles oscillations fall within the predefined range, the method 400B may proceed to 420, where a variable (e.g., an oscillation variable ("Osc")) may be updated to indicate the same. Thereafter, the method 400B may return to 409 and the steps 409-420 may be repeated any suitable number of times, in any suitable order, over time t.

FIG. 4C is a flowchart that illustrates method 400C, a method for determining whether the user's gaze is sufficiently (over a threshold amount) directed toward the horizon. The method 400C may begin at 422, where the "move" variable set at 406 of method 400A may be checked. If the value of the variable indicates the vehicle is not in motion, method 400C may exit at 424. Alternatively, if the value of the move variable indicates the vehicle is in motion, the method 400C may proceed to 424.

At 424, eye gaze data may be captured over time. This eye gaze data may include one or more images and/or videos of the user (e.g., of the user's face, eyes, pupils, etc.) captured over time t. The eye gaze data may be captured by any suitable combination of one or more cameras (e.g., the camera(s) 812 of FIG. 8). The camera(s) may be faced inward toward the user (and in some cases may capture other users in the vehicle as well).

The method 400C may proceed to 426, where the user's gaze may be analyzed to determine an amount by which the user's gaze deviates from the horizon (e.g., over a specified time period 't'). By way of example, the image(s)/video(s) captured at 424 may be analyzed using any suitable image recognition and/or eye track techniques to identify a direction of the user's gaze. Given the known location of the horizon, an amount by which the user's gaze deviates from the horizon may be calculated. In some embodiments, the user's gaze may deviate for over a specified time period 't' before operations for identifying the user's gaze are executed.

At 428, a determination may be made as to whether the amount by which the user's gaze deviates from the horizon exceeds a threshold value over a specified time period t. As an example, the threshold value may be 10 degrees corresponding to 10 degrees in any direction from gazing straight ahead toward the horizon viewable from the front window of the vehicle over a time period (e.g., such as 1 minute, 30 seconds, 5 minutes, etc.). If the amount of deviation does not exceed the threshold, the method 400C may proceed to 430, where a variable (e.g., a gaze variable) may be set to a value indicating the same and the method 400C may proceed back to 422. This loop may continue any suitable number of times over time t so long as the amount of deviation fails to exceed the threshold value.

Alternatively, if the amount of deviation exceeds the threshold value, the method 400C may proceed to 432, where a variable (e.g., a gaze variable ("Gaze")) may be updated to indicate the same. Thereafter, the method 400C may return to 422 and the steps 422-432 may be repeated any suitable number of times, in any suitable order, over time t.

Figure 5:
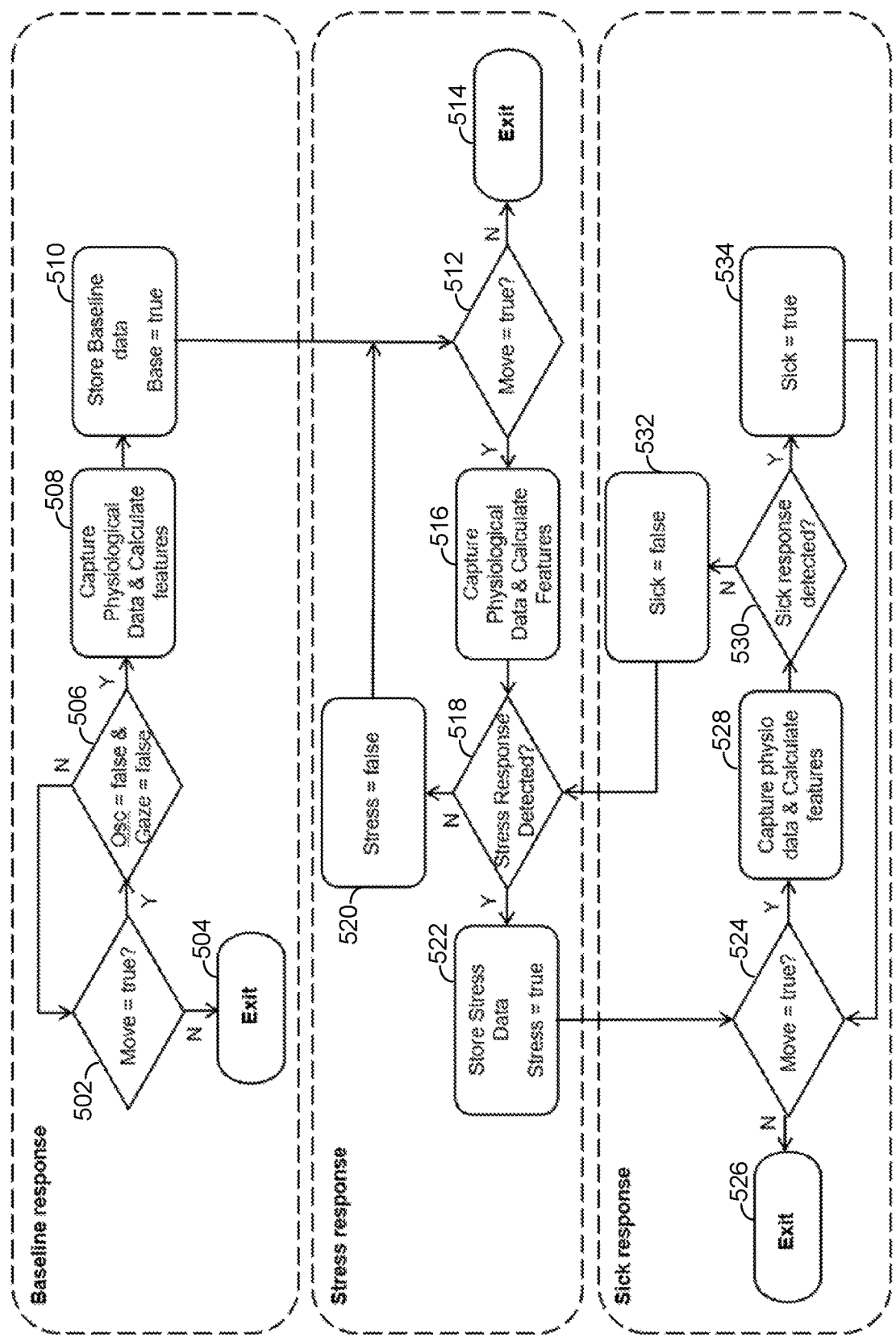
FIG. 5 is a flowchart depicting a method for determining whether a user of a vehicle is experiencing motion sickness, according to an embodiment.

FIG. 5 is a flowchart depicting a method 500 for determining whether a person in a vehicle is experiencing motion sickness, according to an embodiment. Means for performing the method 500 may include one or more hardware and/or software components of a vehicle, such as those illustrated in FIG. 8-10, which is described below.

The method 500 may begin at 502, where the "move" variable set at 406 of method 400A may be checked. If the value of the variable indicates the vehicle is not in motion, method 500 may exit at 504. Alternatively, if the value of the move variable indicates the vehicle is in motion, the method 500 may proceed to 506, where the variables determined by execution of methods 400B and 400C (e.g., a "Osc" variable indicating whether the oscillations of the vehicle fall with the predefined frequency range and a "Gaze" variable indicating whether the user's gaze deviates from the horizon over the threshold amount). If both variables are set to false (or otherwise indicate a negative determination), the method 500 may return to 502. Alternatively, if either (or both) variables are set to true (or otherwise indicate a positive determination), the method 500 may proceed to 508.

At 508, physiological data may be captured and any suitable features may be calculated/identified from such data. By way of example, the physiological data may be collected by any suitable combination of one or more physiological sensor(s) 828 of FIG. 8. Thus, the physiological data may include any suitable data related to heart rate, heart rate variability, blood pressure, blood volume pulse, pulse, oxygen, temperature, skin conductance, galvanic skin response (GSR), electrodermal response (EDR), psychogalvanic reflex (PGR), skin conductance response (SCR), sympathetic skin response (SSR), skin conductance level (SCL) and the like.

Figure 6:
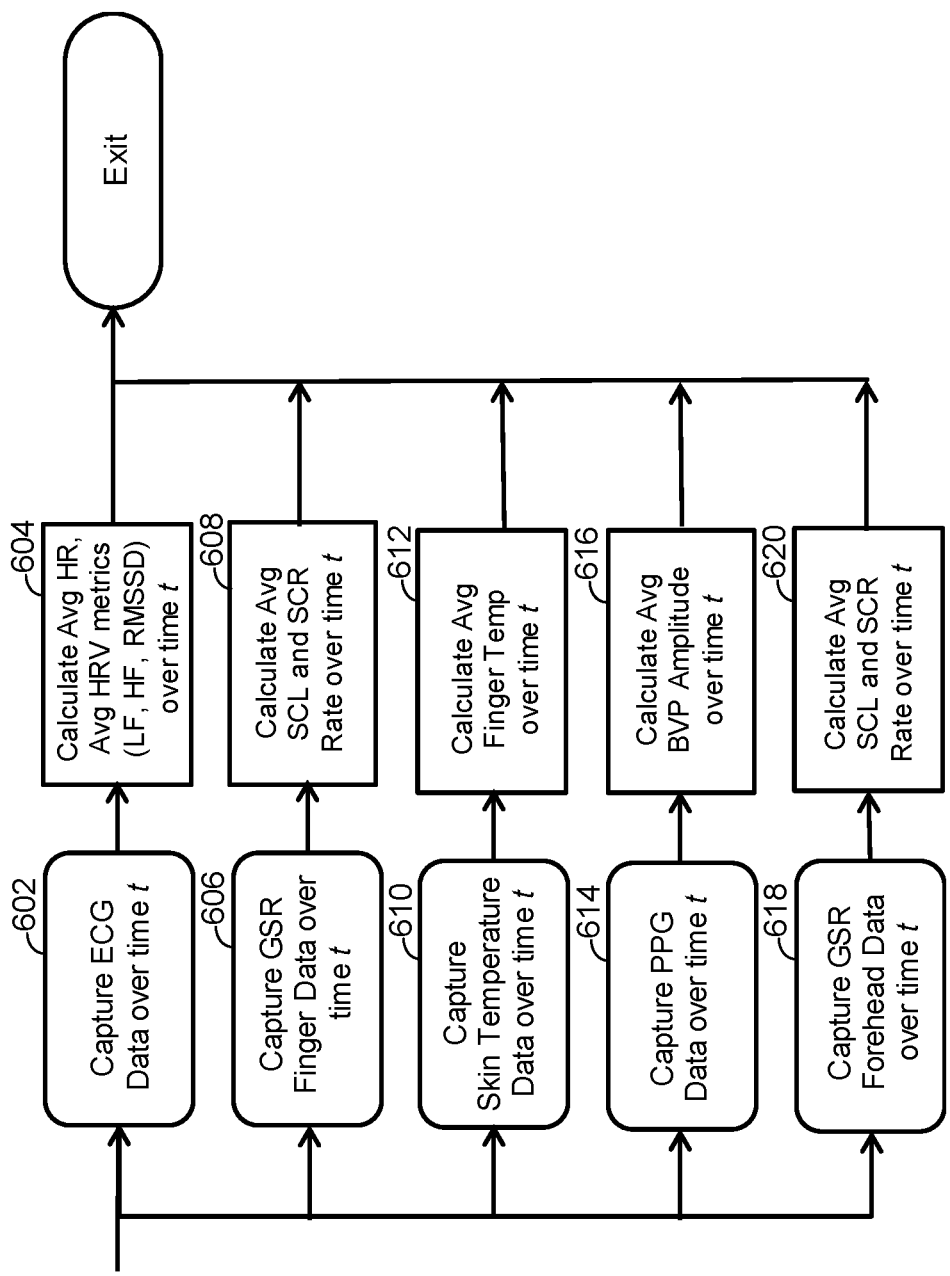
FIG. 6 is a simplified block diagram of a method for calculating a variety of features from collected physiological data, according to an embodiment.

FIG. 6 is a simplified block diagram of a method 600 for calculating a variety of features from collected physiological data, according to an embodiment. In some embodiments, the operations performed at 508 may include the operations of method 600. The steps 602-620 may be performed in any suitable order and/or any suitable number of the operations performed at steps 602-620 may be performed substantially concurrently.

The method 600 may begin 602, where echocardiography data (ECG) data may be captured over time t. The ECG data may be captured by an ECG sensor of the physiological sensor(s) 828 of FIG. 8. At 604, physiological parameters including an average heart rate, average (or actual) heart rate variability metrics (e.g., low frequency (LF), high frequency (HF), root mean square of successive differences (RMSSD)) may be calculated based on the ECG data captured over time t.

The method 600 may proceed 606, where galvanic skin response (GSR) data may be captured over time t. The GSR data may be captured by a GSR sensor of the physiological sensor(s) 828 of FIG. 8. In some embodiments, the GSR data may correspond to a particular part of the body. At 608, physiological parameters including an average skin conductance level and skin conductance response rate may be calculated based on the GSR data captured at 606 over time t.

The method 600 may proceed 610, where skin temperature data may be captured over time t. The skin temperature data may be captured by a temperature sensor of the physiological sensor(s) 828 of FIG. 8. In some embodiments, the temperature data may correspond to a particular part of the body. At 612, physiological parameters including an average temperature (e.g., at a finger where the temperature sensor is placed, a temperature captured at a steering wheel where a sensor is placed, a temperature captured by a wearable device) may be calculated based on the temperatures captured over time t.

The method 600 may proceed 614, where photoplethysmography (PPG) data may be captured over time t. The PPG may be captured by a PPG sensor of the physiological sensor(s) 828 of FIG. 8. At 616, physiological parameters including a blood volume pulse amplitude may be calculated based on the PPG data captured over time t.

The method 600 may proceed 618, where additional GSR data may be captured over time t. The additional GSR data may be captured by another GSR sensor of the physiological sensor(s) 828 of FIG. 8. In some embodiments, the additional GSR sensor may be positioned at the forehead of the user. At 620, physiological parameters including an average skin conductance level and skin conductance response rate may be calculated based on the GSR captured at 618 over time t.

Returning to FIG. 5, the method 500 may proceed from 508 to 510, where the captured physiological data, as well as any features calculated from the same, may be stored as baseline data and a variable indicating that baseline data exists may be set. Steps 502-510 may correspond to block 116 of FIG. 1.

At 512, where the "move" variable set at 406 of method 400A may be again checked. If the value of the variable indicates the vehicle is not in motion, method 500 may exit at 514. Alternatively, if the value of the move variable indicates the vehicle is in motion, the method 500 may proceed to 516, where subsequent physiological data may be captured and corresponding features may be calculated. In some embodiments, the operations performed at 516 may include execution of the method 600 of FIG. 6.

At 518, a determination may be made as to whether the user has experienced a stress response (e.g., as indicated in FIG. 2). In some embodiments, this determination may made based at least in part on comparing the physiological data and/or corresponding physiological features (e.g., heart rate, BVP, RMSSD, LF, HF, LF/HF, GSR values, temperatures at particular locations of the body, etc.) to a predefined set of physiological feature values associated with a stress response and/or by determining that each feature has remained substantially constant or changed (e.g., increased or decreased) in a predefined manner with respect to the baseline data stored at 510. For example, a predefined set of physiological features could indicate that an increase in heart rate and GSR at a finger signals onset of the stress response. A comparison of the physiological data and/or features to the predefined set may indicate a stress response when the user's data/features indicates a similar increase. In other embodiments, the determination that a user is experiencing a stress response may be made based at least in part on providing the physiological data and/or the corresponding physiological features calculated at 516 as input to a machine learning model trained to identify input data as being either indicative of a stress response or not indicative of a stress response.

In some embodiments, a machine learning model utilized at 518 may be trained using supervised learning techniques and a training data set to classify new input data (e.g., physiological data and/or features derived from such data) as being indicative of the user experiencing a stress response or not. In some embodiments, the training data set may include any suitable number of examples including any suitable combination of physiological data and or physiological features derived from such data for which a classification (e.g., stress response=true, stress response=false) is known. The training data set may include any suitable number of examples that are indicative of stress response and/or examples that are not indicative of a stress response. The model may be trained using supervised learning algorithms such as regression algorithms (e.g., linear regression, logistic regression, etc.), decision trees, random forest, neural networks, naive Bayes, k-nearest neighbor, and the like. Once the model is trained, new data (e.g., physiological data and/or corresponding physiological feature derived from such data) may be provided to the model, and in response, the model may provide a value (e.g., true, false) that may be considered a determination as to whether the user is experiencing a stress response.

If it is determined at 518 that the user has not experienced a stress response, the method may proceed to 520, where a stress variable may be set (e.g., to false or otherwise indicate a negative determination) and the method 500 may return to 512. Alternatively, if it is determined at 518 that the user has experienced a stress response, the method 500 may proceed to 522, where the stress data (e.g., the data collected and/or calculated at 516) may be stored and/or the stress variable may be set (e.g., to true, or otherwise indicate a positive determination). The steps 512-522 may correspond to block 118 of FIG. 1.

The method 500 may proceed to 524, where the "move" variable set at 406 of method 400A may be again checked. If the value of the variable indicates the vehicle is not in motion, method 500 may exit at 526. Alternatively, if the value of the move variable indicates the vehicle is in motion, the method 500 may proceed to 528, where additional physiological data may be captured and corresponding physiological features may be calculated. In some embodiments, the operations performed at 528 may include execution of the method 600 of FIG. 6.

At 530, a determination may be made as to whether the user has experienced a sick response (e.g., the sick response indicated in FIG. 2). In some embodiments, this determination may made based at least in part on comparing the physiological data and/or corresponding physiological features (e.g., heart rate, BVP, RMSSD, LF, HF, LF/HF, GSR values, temperatures at particular locations of the body, etc.) to a predefined set of physiological feature values associated with a sick response and/or by determining that each feature has remained substantially constant or changed (e.g., increased or decreased) in a predefined manner with respect to the stress data stored at 522. For example, a predefined set of physiological features could indicate that an increase of GSR at a forehead (e.g., after an increase of heart rate and GSR at a finger as indicated in FIG. 2) signals onset of the sick response. A comparison of the physiological data and/or features to the predefined set may indicate a sick response when the user's data/features indicates a similar increase. In other embodiments, the determination that a user is experiencing a sick response may be made based at least in part on providing the physiological data and/or the corresponding physiological features calculated at 528 as input to a machine learning model trained to identify input data as being either indicative of a sick response or not indicative of a sick response.

In some embodiments, a machine learning model utilized at 530 may be trained using supervised learning techniques and a training data set to classify new input data (e.g., physiological data and/or features derived from such data) as being indicative of the user experiencing a sick response or not. In some embodiments, the training data set may include any suitable number of examples including any suitable combination of physiological data and or physiological features derived from such data for which a classification (e.g., sick response=true, sick response=false) is known. The training data set may include any suitable number of examples that are indicative of sick response and/or examples that are not indicative of a sick response. The model may be trained using supervised learning algorithms such as regression algorithms (e.g., linear regression, logistic regression, etc.), decision trees, random forest, neural networks, naive Bayes, k-nearest neighbor, and the like. Once the model is trained, new data (e.g., physiological data and/or corresponding physiological feature derived from such data) may be provided to the model, and in response, the model may provide a value (e.g., true, false) that may be considered a determination as to whether the user is experiencing a sick response.

If it is determined at 530 that the user has not experienced a sick response, the method may proceed back to 518. Alternatively, if it is determined at 530 that the user has experienced a sick response, the method 500 may proceed to 534, where a sick variable may be set (e.g., to true, or otherwise indicate a positive determination). The steps 524-534 may correspond to block 120 of FIG. 1. In some embodiments, the physiological data and/or features captured/calculated at 528 may be stored for subsequent use.

Figure 7:
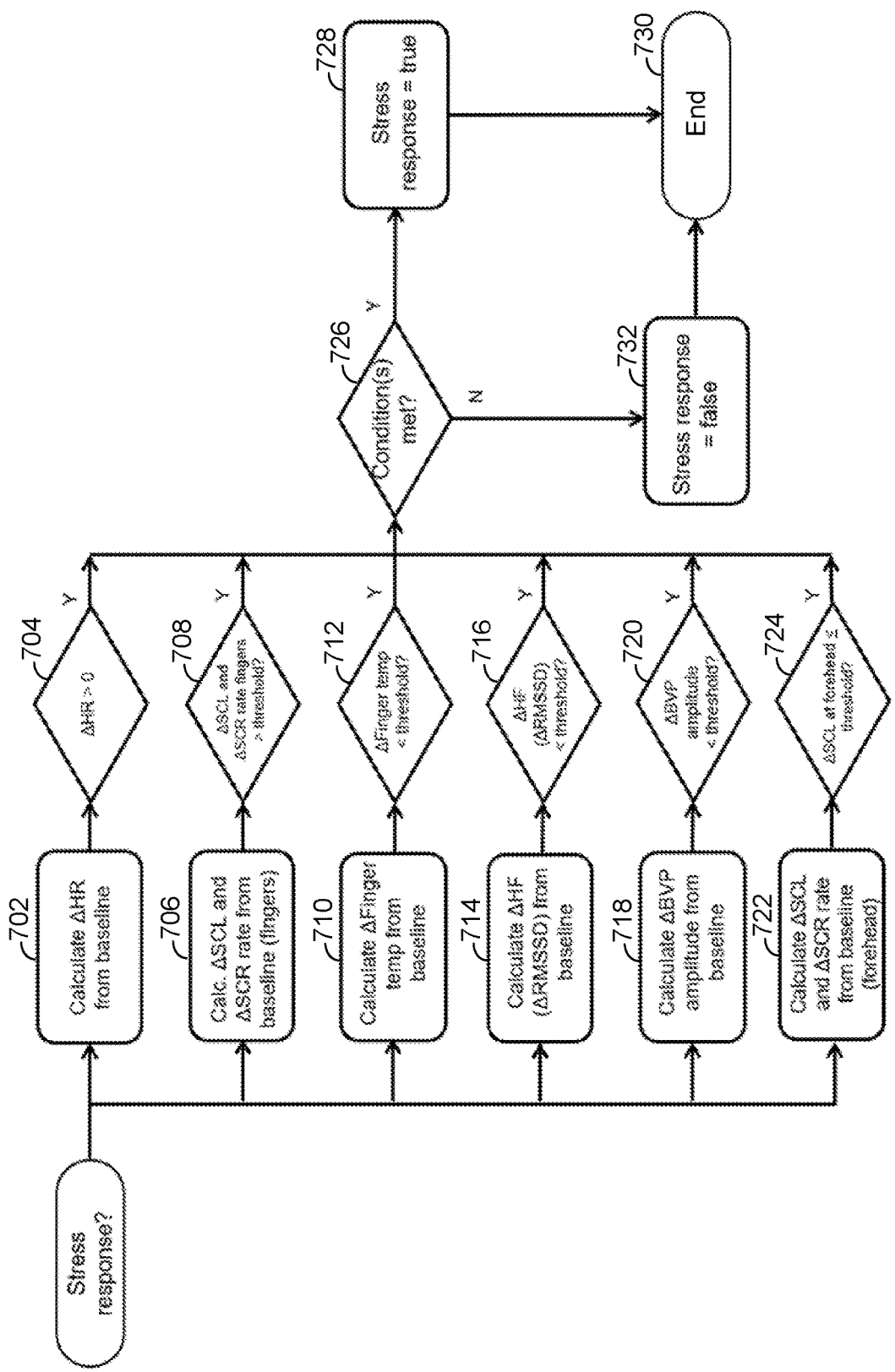
FIG. 7 is a simplified block diagram of a method for determining whether a stress response has occurred, according to an embodiment.

FIG. 7 is a simplified block diagram of a method 700 for determining whether a stress response has occurred, according to an embodiment. Prior to execution of method 700, the method 600 can be executed at a first time to calculate a variety of features from collected physiological data corresponding to collecting baseline data. The method 600 can be executed at a second time (e.g., a second time that is later than the first) to calculate a variety of features from collected physiological data corresponding to collecting current data. Method 700 may begin after baseline data and current data have been collected.

The method 700 may begin at 702, where a difference between the baseline heart rate and the current heart rate may be calculated. At 704, if the difference in heart rate identified at 702 exceeds a predetermined heart rate threshold, it may be determined that the difference in heart rate indicates one feature of a stress response. If the difference in heart rate does not exceed the predetermined heart rate threshold, it may be determined that that feature of the stress response is not indicated.

At 706, a difference between a current SCL and the baseline SCL at the fingers (or another location) and a difference between a current SCR rate and the baseline SCR rate at the fingers (or another location) may be calculated. At 710, if both the difference in SCL and the difference in SCR rate exceed a predetermined threshold, it may be determined that a particular feature of a stress response is indicated. If either or both differences fail to exceed the threshold, it may be determined that that particular feature of the stress response is not indicated.

At 710, a difference between the baseline skin temperature at the fingers (or another location) and the current skin temperature at the fingers (or another location) may be calculated. At 712, if the difference identified at 710 is less than a corresponding predetermined temperature threshold, it may be determined a feature of a stress response is indicated. If the difference identified at 710 is equal to or exceeds the corresponding predetermined temperature threshold, it may be determined that that feature of the stress response is not indicated.

At 714, a difference between a current HF and the baseline HF or a difference between a current RMSSD and a baseline RMSSD may be calculated. At 716, if either of the difference HF or the difference in RMSSD are less than a corresponding predetermined threshold, it may be determined that a particular feature of a stress response is indicated. If neither difference is determined to be less than the corresponding predetermined threshold, then it may be determined that that particular feature of a stress response is not indicated.

At 718, a difference between the baseline BVP and the current BVP may be calculated. At 720, if the difference in BVP identified at 716 is less than a corresponding predetermined BVP threshold, it may be determined that the difference in BVP indicates one feature of a stress response. If the difference in BVP is equal to or exceeds the predetermined BVP threshold, it may be determined that that feature of the stress response is not indicated.

At 722, a difference between a current SCL and the baseline SCL at the forehead and a difference between a current SCR rate and the baseline SCR rate at the forehead may be calculated. At 724, if both the difference in SCL and the difference in SCR rate are less than or equal to a predetermined threshold, it may be determined that a feature of a stress response is indicated. If either or both differences exceed the threshold, it may be determined that that particular feature of the stress response is not indicated.

At 726, a determination may be made whether a set of conditions are met based at least in part on the determinations made at 704, 708, 712, 716, 720, and 724. By way of example, a set of threshold conditions for determining a stress response has occurred may include determining that the heart rate has changed (e.g., see 704), determining that the SCR rate has changed, and at least one other affirmative determination from the determinations made at 708, 712, 716, 720, and/or 724. In some embodiments, the threshold conditions needed for the determination at 726 may be user configurable. If the threshold condition(s) are met, a determination may be made at 728 that the stress response has occurred and the method 700 may end at 730. If the threshold is not met or exceeded, then a determination may be made at 732 that the stress response has not occurred and the method 700 may end at 730.

It should be appreciated that more or fewer difference values may be calculated than the number shown in FIG. 7. It should also be appreciated that the calculations of 702, 706, 710, 714, 718, 722 may be performed in any suitable order. In some embodiments, the features calculated from the collected physiological data corresponding to the current data may be stored for subsequent use. This data may be referred to as "stress data." For example, if the determination is made that the stress response is indicated (e.g., at 728), the physiological data and the features calculated from it corresponding to the "current data" may be stored for subsequent use. This data may be referred to below as "stress data."

Figure 8:
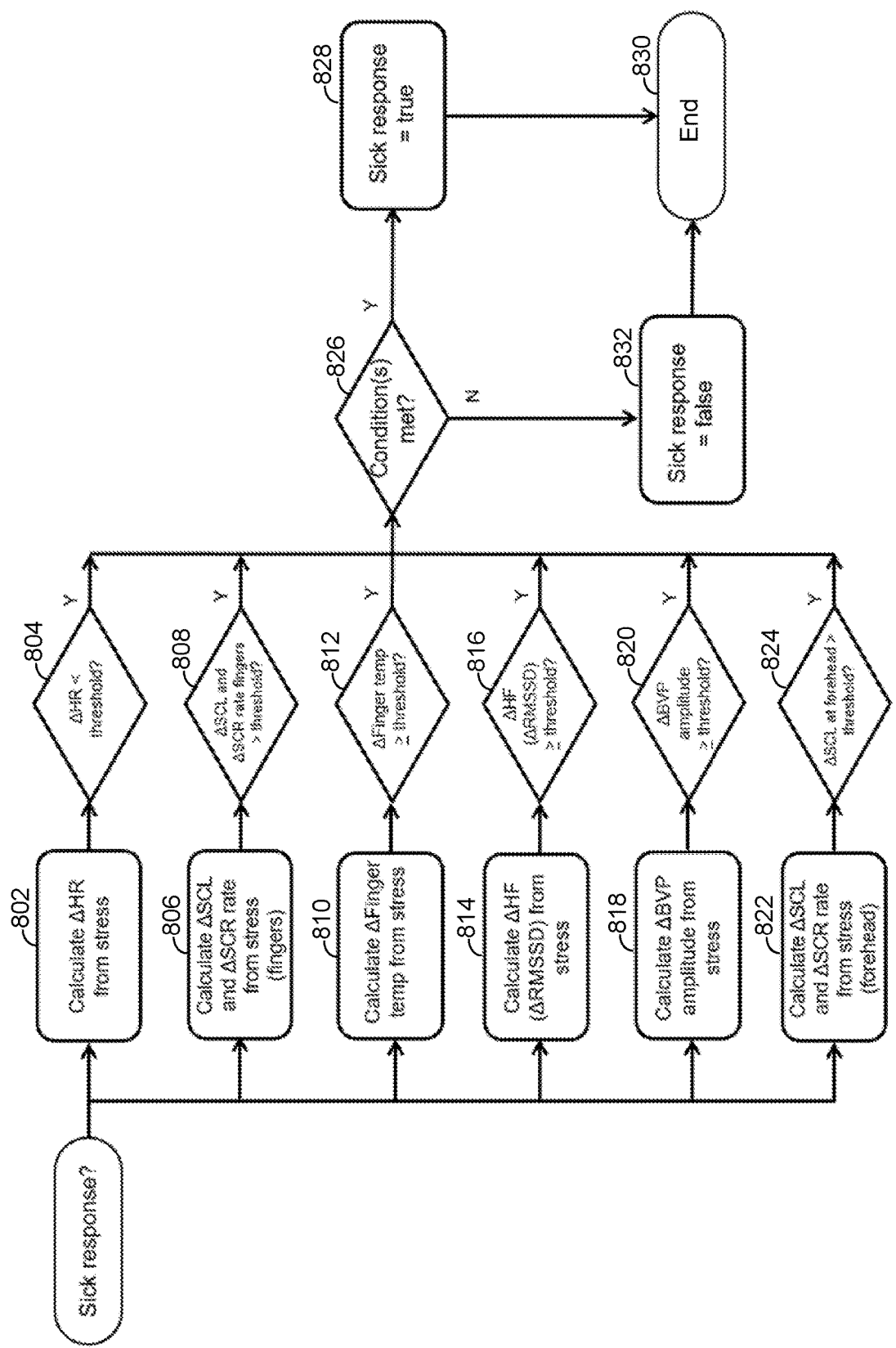
FIG. 8 is a simplified block diagram of a method for determining whether a sick response has occurred, according to an embodiment.

FIG. 8 is a simplified block diagram of a method 800 for determining whether a sick response has occurred, according to an embodiment. In some embodiments, method 800 may be executed after the execution of method 700 of FIG. 7. Method 600 may be performed once again to collect physiological data and to calculate features from that physiological data. This may now be considered the current data. For illustrative purposes, time Ts may refer to a time at which the stress response of FIG. was determined to have occurred.

The method 800 may begin at 802, where a difference between the heart rate corresponding time Ts and the heart rate of the current data may be calculated. At 804, if the difference in heart rate identified at 802 is less than a predetermined heart rate threshold, it may be determined that the difference indicates one feature of a sick response. If the difference in heart rate is equal to or exceeds the predetermined heart rate threshold, it may be determined that that feature of the sick response is not indicated.

At 806, a difference between the current SCL at the fingers and the SCL at the fingers at time Ts and a difference between a current SCR rate and the SCR rate at the fingers at time Ts may be calculated. At 808, if both the difference in SCL and the difference in SCR rate exceed a predetermined threshold, it may be determined that a particular feature of a sick response is indicated. If either or both differences are equal to or fail to exceed the threshold, it may be determined that that particular feature of the sick response is not indicated.

At 810, a difference between the skin temperature at the fingers at time Ts and the current skin temperature at the fingers may be calculated. At 812, if the difference identified at 810 is equal to or exceeds corresponding predetermined temperature threshold, it may be determined a feature of a sick response is indicated. If the difference identified at 710 is less than the corresponding predetermined temperature threshold, it may be determined that that feature of the sick response is not indicated.

At 814, a difference between a current HF and the HF at time Ts or a difference between a current RMSSD and the RMSSD at time Ts may be calculated. At 816, if either the difference HF or the difference in RMSSD is equal to or exceeds a corresponding predetermined threshold, it may be determined that a particular feature of a sick response is indicated. If neither HF nor RMSSD are equal to or exceeding the corresponding predetermined threshold, it may be determined that that particular feature of the sick response is not indicated.

At 818, a difference between the current BVP and the BVP at time Ts may be calculated. At 820, if the difference in BVP identified at 818 is greater than or equal to corresponding predetermined BVP threshold, it may be determined that the difference in BVP indicates one feature of a sick response. If the difference in BVP is less than the predetermined BVP threshold, it may be determined that that feature of the sick response is not indicated.

At 822, a difference between a current SCL at the forehead and the SCL at the forehead at time Ts and a difference between a current SCR rate at the forehead and the SCR rate at the forehead at time Ts may be calculated. At 824, if both the difference in SCL and the difference in SCR rate greater than a predetermined threshold, it may be determined that a feature of a sick response is indicated. If either or both differences are equal to or exceed the threshold, it may be determined that that particular feature of the sick response is not indicated.

At 826, a determination may be made whether a set of conditions are met based at least in part on the determinations made at 804, 808, 812, 816, 820, and 824. By way of example, a set of threshold conditions for determining whether a sick response has occurred may include determining that the SCR rate at the forehead has changed and at least two other affirmative determinations from the determinations made at 804, 808, 812, 816, 820, and/or 824. In some embodiments, the threshold conditions needed for the determination at 826 may be user configurable. If the threshold condition(s) are met, a determination may be made at 828 that the sick response has occurred and the method 800 may end at 830. If the threshold is not met or exceeded, then a determination may be made at 832 that the stress response has not occurred and the method 800 may end at 830.

It should be appreciated that more or fewer difference values may be calculated than the number shown in FIG. 8. It should also be appreciated that the calculations of 802, 806, 810, 814, 818, 822 may be performed in any suitable order. In some embodiments, method 800 may not be executed unless the execution of method 700 resulted in a determination that a stress response occurred.

Figure 9:
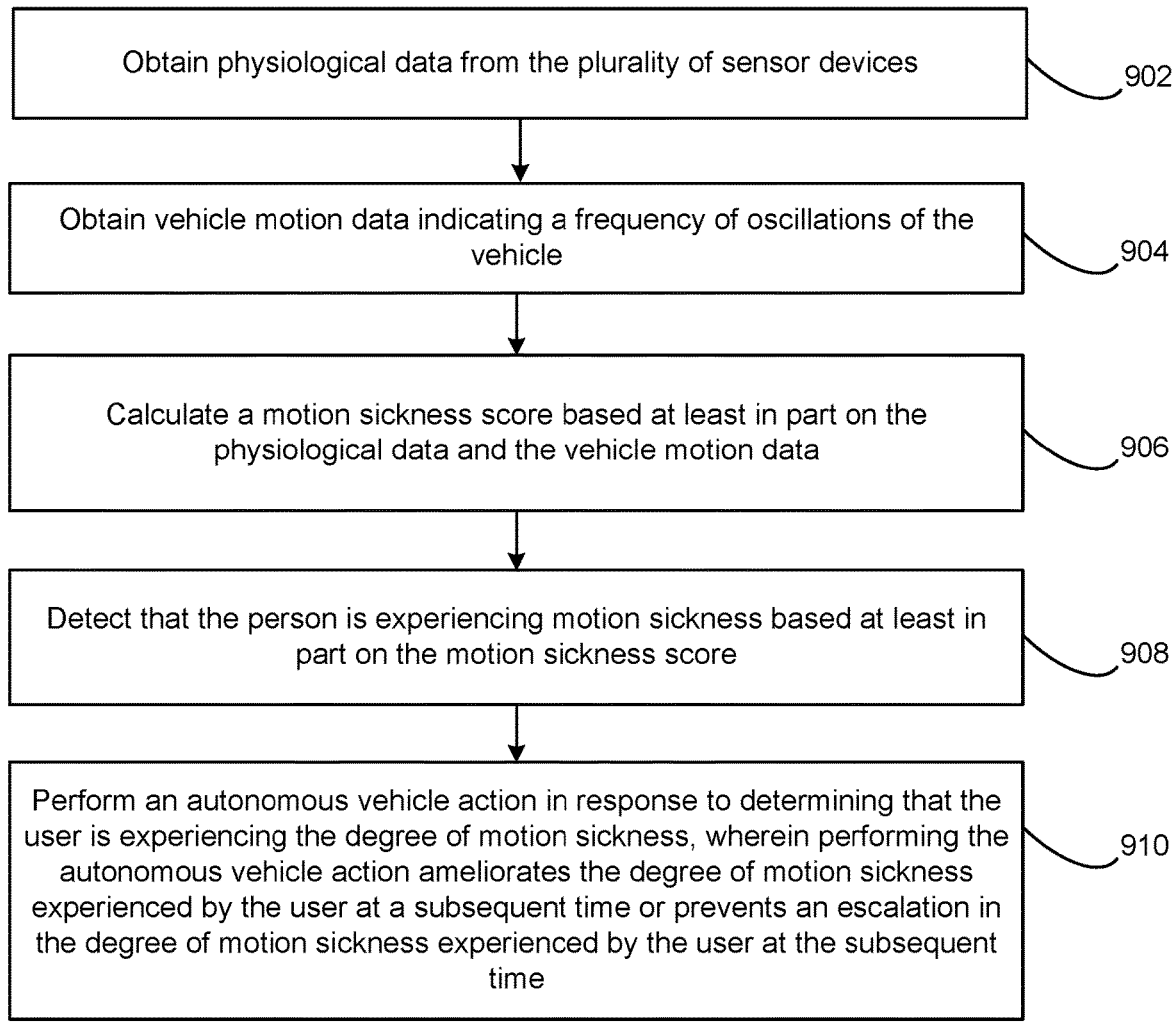
FIG. 9 is a flow diagram of a method for preventing or ameliorating motion sickness of a user within a vehicle, according to an embodiment.

FIG. 9 is a flow diagram for a method 900 for preventing or ameliorating motion sickness of a user within a vehicle, according to an embodiment. Means for performing the method 900 may include one or more hardware and/or software components of a vehicle, such as those illustrated in FIG. 10-12, which is described below. Method 700 may be performed by a computing device (e.g., the vehicle 1000, the processor(s) 1002 of FIG. 10, etc.). In some embodiments, instructions for the method 900 may be stored in a non-transitory computer readable medium (e.g., memory 1004 of FIG. 10) and one or more processors (e.g., the processor(s) 1002 of FIG. 10) may execute the instructions to perform the operations of method 900. In some embodiments, the operations of method 900 are performed by the one or more processor(s) 1002 of FIG. 10 by executing code associated with motion sickness detection engine 1030 of FIG. 10.

Figure 10:
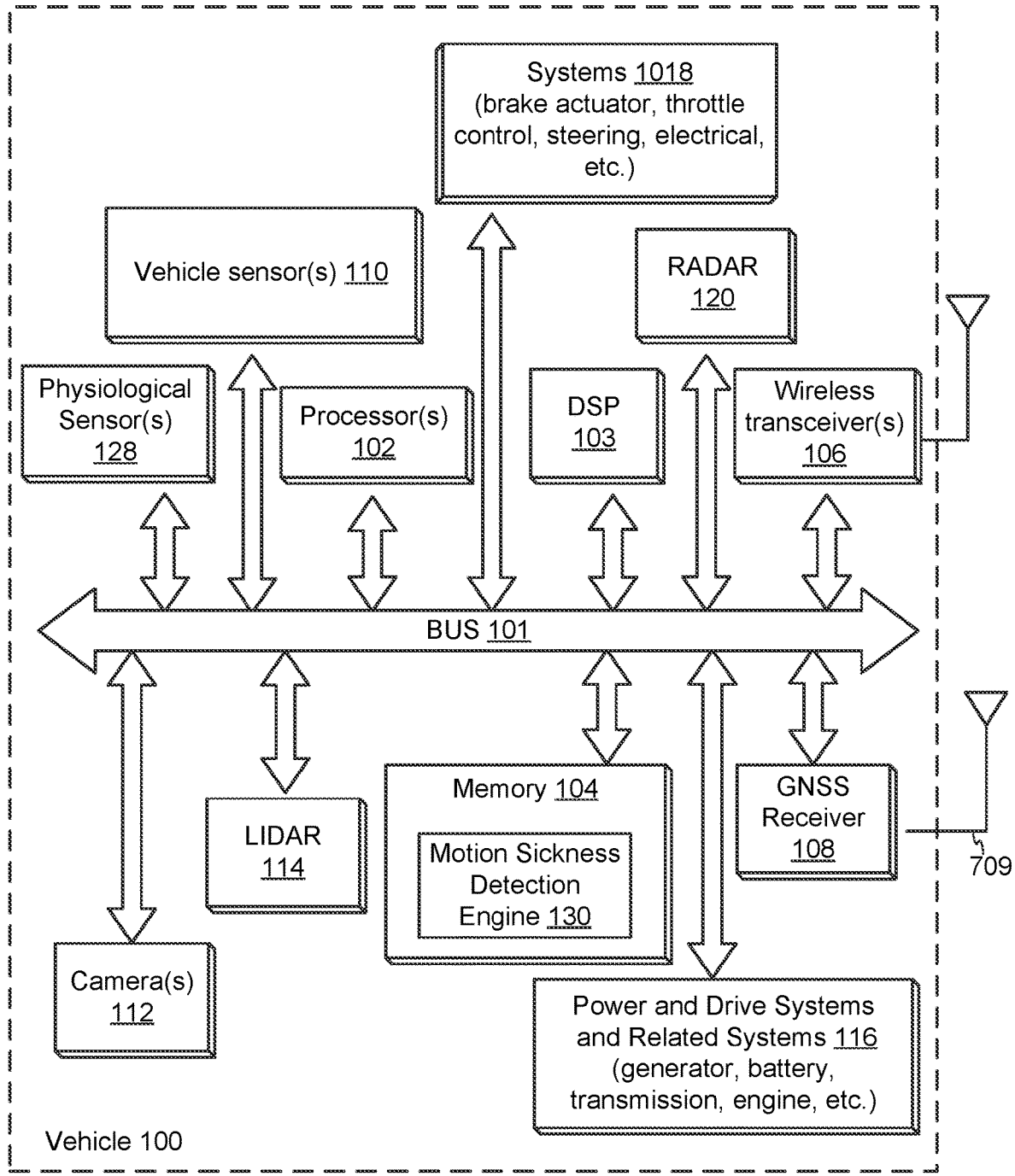
FIG. 10 comprises a functional block diagram of a vehicle, according to an embodiment.

Method 900 may begin at block 902, wherein physiological data may be obtained (e.g., by the one or more processor(s) 1002) from a plurality of sensor devices (e.g., the physiological sensor(s) 1028 of FIG. 10).

At block 904, vehicle motion data of the vehicle (e.g., the vehicle 1000) may be obtained (e.g., by the one or more processor(s) 1002 from, for example, the vehicle sensor(s) 1010 of FIG. 10).

At block 906, a motion sickness score may be calculated (e.g., by the processor(s) 902) based at least in part on the physiological data and the vehicle motion data. Although not depicted in FIG. 9, it may be appreciated that the motion sickness score may be calculated further based at least in part on eye gaze data. In some embodiments, the motion sickness score may be calculated based at least in part on a mathematical function wherein particular data may be weighted more heavily than other data. In some embodiments, the motion sickness score may be calculated by providing the physiological data and/or the vehicle motion data (and/or features derived from the same and/or eye gaze data) as input to one or more machine learning models (e.g., one or more machine learning models maintained by and/or accessible to one or more processor(s) 1002. The instructions associated with the motion sickness detection engine 1030, when executed by the processor(s) 1002, may cause any of the machine learning operations discussed herein to be performed.

At block 908, a degree of motion sickness that the user is experiencing may be detected (e.g., by the one or more processor(s) 1002) based at least in part on the motion sickness score.

At block 910, an autonomous vehicle action may be performed (e.g., by the one or more processor(s) 1002) in response to determining that the user is experiencing the degree of motion sickness. In some embodiments, performing the autonomous vehicle action ameliorates the degree of motion sickness experienced by the user at a subsequent time or prevents an escalation in the degree of motion sickness experienced by the user at the subsequent time. By way of example, an autonomous vehicle action may comprise slowing the vehicle down, modifying a route, performing less aggressive turns, maintaining a more constant heading, or any combination of the above.

Figure 11:
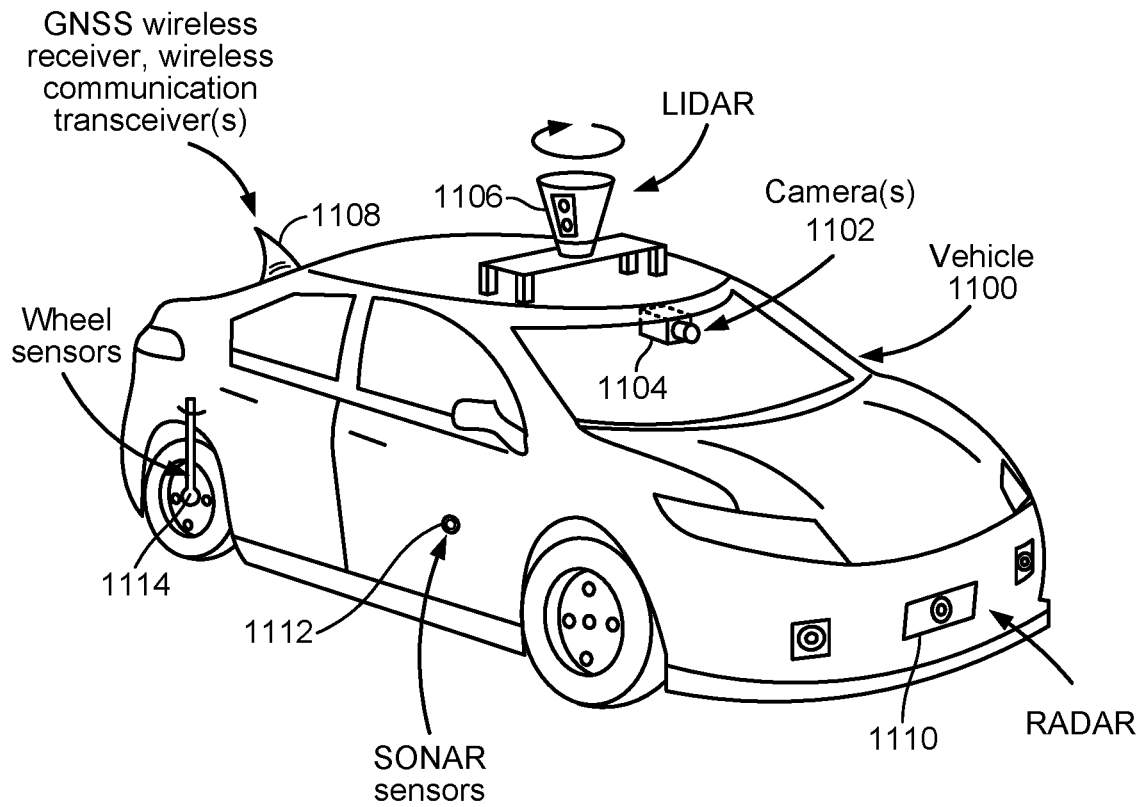
FIG. 11 is a schematic diagram of various hardware and software components of a vehicle, according to an embodiment.
Figure 12:
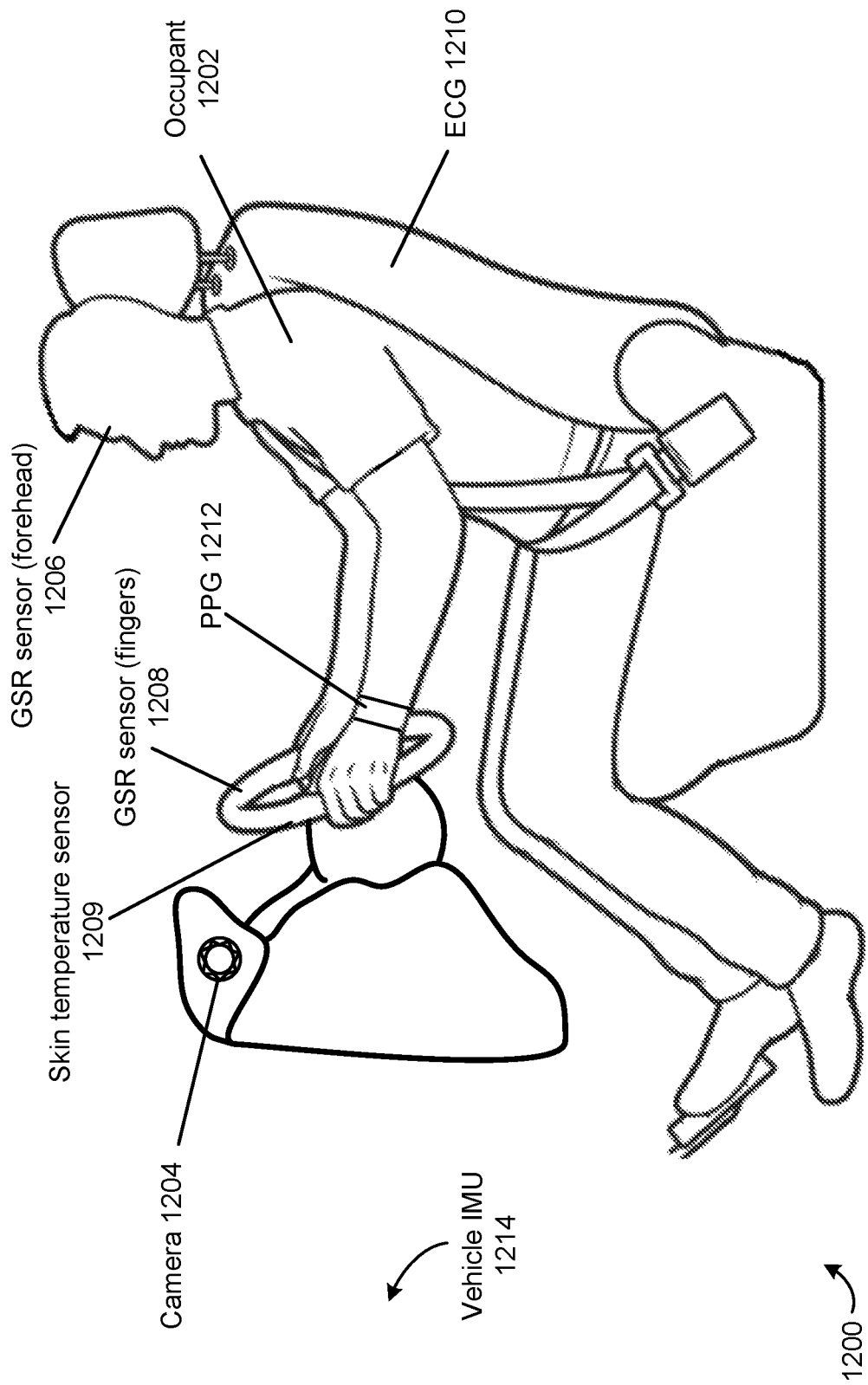
FIG. 12 is a schematic diagram depicting an example configuration of a number of cameras positioned to collect eye gaze data and a number of physiological sensors configured to collect physiological data of a user in a vehicle, according to an embodiment.

FIGS. 10-12 are illustrations of systems, structural devices, vehicle components, and other devices, components, and systems that can be used to implement the techniques provided herein for detecting a degree of motion sickness that a person may be experiencing while traveling in an autonomously driven vehicle.

FIG. 10 comprises a functional block diagram of a vehicle 1000, according to an embodiment. The methods discussed herein may be performed in relation to a person traveling within vehicle 800, as described in the embodiments above. Moreover, hardware and/or software components for executing the blocks shown in FIGS. 1-9 are described in more detail below. The vehicle 1000 may comprise for example, a car, bus, truck, motorcycle and/or other motorized vehicle that may, at least in part, be driven autonomously.

As shown in FIG. 10, vehicle 1000 may include a variety of software and hardware components connected via bus 1001. For example, the vehicle 1000 may include one or more processor(s) 1002 and memory 1004. Memory 1004 may include executable instructions, executable by the processor(s) 1002, to perform autonomous driving activities including, but not limited to, external object sensing and classification, prediction and planning, and maneuver execution. Vehicle 1000 may include one or more wireless transceivers, such as wireless transceiver(s) 1006, for transmitting and receiving data via various means, protocols and standards, such as via SAE or European Telecommunications Standards Institute (ETSI) CV2X messages and data elements or other wireless and wireless protocols. In some embodiments, the wireless transceiver(s) 1006 may be configured to transmit and receive data messages and elements via a short-range wireless communications protocol (e.g., Bluetooth®, Bluetooth Low Energy®, etc.), and/or via a local and/or wide area network, and/or via a cellular network, and/or via any suitable wireless network. Of course, it should be understood that these are merely examples of networks that may be utilized by the vehicle 1000 over a wireless link, and claimed subject matter is not limited in this respect. In an embodiment, wireless transceiver(s) 1006 may comprise various combinations of WAN, WLAN, and/or PAN transceivers. In an embodiment, wireless transceiver(s) 1006 may also comprise a Bluetooth transceiver, a ZigBee transceiver, or other PAN transceiver.

In some embodiments, the vehicle 1000 may include a Global Navigation Satellite System (GNSS) receiver 1008. The GNSS receiver 1008 may be configured to receive and digitally process signals from a navigation satellite (and/or other vehicles) in order to provide position, velocity, and time of the receiver. The GNSS receiver 1008 may include hardware and/or software components. In an embodiment, GNSS signals from GNSS Satellites received by the GNSS receiver 1008 are utilized by vehicle 1000 for location determination and/or for the determination of GNSS signal parameters and demodulated data. In an embodiment, signals received by wireless transceiver(s) 806 are used for location determination, alone or in combination with GNSS signals received by the GNSS receiver 1008.

Examples of network technologies that may support wireless transceiver(s) 1006 are GSM, CDMA, WCDMA, LTE, 5G or New Radio Access Technology (NR), HRPD, and V2X car-to-car communication. As noted, V2X communication protocols may be defined in various standards such as SAE and ETS-ITS standards. GSM, WCDMA and LTE are technologies defined by 3GPP. CDMA and HRPD are technologies defined by the $3^{rd}$ Generation Partnership Project II (3GPP2). WCDMA is also part of the Universal Mobile Telecommunications System (UMTS) and may be supported by an HNB.

Wireless transceiver(s) 1006 may communicate with communications networks via WAN wireless base stations which may comprise deployments of equipment providing subscriber access to a wireless telecommunication network for a service (e.g., under a service contract). Here, a WAN wireless base station may perform functions of a WAN or cell base station in servicing subscriber devices within a cell determined based, at least in part, on a range at which the WAN wireless base station is capable of providing access service. Examples of WAN base stations include GSM, WCDMA, LTE, CDMA, HRPD, Wi-Fi, Bluetooth, WiMAX, 5G NR base stations. In an embodiment, further wireless base stations may comprise a WLAN and/or PAN transceiver.

In an embodiment, vehicle 1000 may contain one or more camera(s) 1012. In an embodiment, the camera(s) 1012 may comprise a camera sensor and mounting assembly. Different mounting assemblies may be used for different cameras on vehicle 1000. For example, front facing cameras may be mounted in the front bumper, in the stem of the rear-view mirror assembly or in other front facing areas of the vehicle 1000. Rear facing cameras may be mounted in the rear bumper/fender, on the rear windshield, on the trunk or other rear facing areas of the vehicle. The side facing mirrors may be mounted on the side of the vehicle such as being integrated into the mirror assembly or door assemblies. The cameras may provide object detection and distance estimation, particularly for objects of known size and/or shape (e.g., a stop sign and a license plate both have standardized size and shape) and may also provide information regarding rotational motion relative to the axis of the vehicle such as during a turn. When used in concert with the other sensors, the cameras may both be calibrated through the use of other systems such as through the use of LIDAR, wheel tick/distance sensors, and/or GNSS to verify distance traveled and angular orientation. The cameras may similarly be used to verify and calibrate the other systems to verify that distance measurements are correct, for example by calibrating against known distances between known objects (landmarks, roadside markers, road mile markers, etc.) and also to verify that object detection is performed accurately such that objects are accordingly mapped to the correct locations relative to the car by LIDAR and other system. Similarly, when combined with, for example, accelerometers, impact time with road hazards, may be estimated (elapsed time before hitting a pot hole for example) which may be verified against actual time of impact and/or verified against stopping models (for example, compared against the estimated stopping distance if attempting to stop before hitting an object) and/or maneuvering models (verifying whether current estimates for turning radius at current speed and/or a measure of maneuverability at current speed are accurate in the current conditions and modified accordingly to update estimated parameters based on camera and other sensor measurements).

In some embodiments, camera(s) 1012 may be inward facing (e.g., facing one or more passengers of the vehicle. The camera(s) 1012 may be utilized to capture one or more images and/or video(s) (herein referred to as "eye gaze data") of at least some portion of one or more of the vehicle occupants. By way of example, camera(s) 1012 may be positioned to capture images/video (e.g., periodically, according to a schedule, every second, etc.) of some portion of the face (e.g., the eyes) of one or more of the vehicle's occupants.

Vehicle sensor(s) 1010 may include any suitable number of accelerometers, gyros, and/or magnetometers. In some embodiments, the vehicle sensor(s) 1010 may be part of an inertial measurement unit of the vehicle 1000. The vehicle sensor(s) 1010 may be utilized to provide and/or verify motion and directional information, to monitor wheel and drive train performance, and/or to measure amplitude and frequency of oscillations of the vehicle 1000 and/or parts of the vehicle 1000. By way of example, an accelerometer (e.g., a 3-axis accelerometer) can measure vibrations of the vehicle 1000 such as movement or mechanical oscillation about an equilibrium position of a component of the vehicle 1000. Accelerometers, in an embodiment, may also be utilized to verify actual time of impact with road hazards such as pot holes relative to predicted times based on existing stopping and acceleration models as well as steering models. Gyros and magnetometers of the vehicle sensor(s) 1010 may, in an embodiment, be utilized to measure rotational status of the vehicle as well as orientation relative to magnetic north, respectively, and to measure and calibrate estimates and/or models for turning radius at current speed and/or a measure of maneuverability at current speed, particularly when used in concert with measurements from other external and internal sensors such as other sensors such as speed sensors, wheel tick sensors, and/or odometer measurements. In some embodiments, vehicle sensor(s) 1010 may be configured to measure oscillations and/or oscillation frequency corresponding to motions performed by the vehicle 1000.

The vehicle 1000 may include LIDAR 1014. LIDAR 1014 may use pulsed laser light to measure ranges to objects. While camera(s) 1012 can provide object detection, LIDAR 1014 may provide a means to detect the distances (and orientations) of the objects with more certainty, especially in regard to objects of unknown size and shape. LIDAR 1014 measurements may also be used to estimate rate of travel, vector directions, relative position and stopping distance by providing accurate distance measurements and delta distance measurements.

In an embodiment, power and drive systems and related systems 1016 (generator, battery, transmission, engine) and systems 1018 (brake, actuator, throttle control, steering, and electrical) may be controlled by the processor(s) 1002 and/or hardware or software or by an operator of the vehicle or by some combination thereof. The systems 1018 and power and drive systems and related systems 1016 may be utilized in conjunction with performance parameters and operational parameters, to enable autonomously (and manually, relative to alerts and emergency overrides/braking/stopping) driving and operating a vehicle 1000 safely and accurately, such as to safely, effectively and efficiently merge into traffic, stop, accelerate and otherwise operate the vehicle 800. In an embodiment, input from the various sensor systems such as camera(s) 1012, vehicle sensor(s) 1010 (including accelerometers, gyros, manometers, etc.), LIDAR 1014, GNSS receiver 1008, RADAR 1020, input, messaging and/or measurements from wireless transceiver(s) 1006 or various combinations thereof, may be utilized by processor(s) 1002 and/or DSP 1003 or other processing systems to control power and drive systems and related systems 1016 and systems 1018.

GNSS receiver 1008 may be utilized to determine position relative to the earth (absolute position) and, when used with other information such as measurements from other objects and/or mapping data, to determine position relative to other objects such as relative to other vehicles and/or relative to the road surface. To determine position, the GNSS receiver 1008, may receive RF signals from one or more GNSS satellites using one or more antenna(s) 1009. The GNSS receiver 1008 may support one or more GNSS constellations as well as other satellite-based navigation systems. For example, in an embodiment, GNSS receiver 1008 may support global navigation satellite systems such as GPS, the GLONASS, Galileo, and/or BeiDou, or any combination thereof. In an embodiment, GNSS receiver 1008 may support regional navigation satellite systems such as NavIC or QZSS or a combination thereof as well as various augmentation systems (e.g., Satellite Based Augmentation Systems (SBAS) or ground based augmentation systems (GBAS)) such as Doppler Orbitography and Radio-positioning Integrated by Satellite (DORIS) or wide area augmentation system (WAAS) or the European geostationary navigation overlay service (EGNOS) or the multi-functional satellite augmentation system (MSAS) or the local area augmentation system (LAAS). In an embodiment, GNSS receiver 1008 and antenna(s) 1009 may support multiple bands and sub-bands such as GPS L1, L2 and L5 bands, Galileo E1, E5, and E6 bands, Compass (BeiDou) B1, B3 and B2 bands, GLONASS G1, G2 and G3 bands, and QZSS L1C, L2C and L5-Q bands.

The GNSS receiver 1008 may be used to determine location and relative location which may be utilized for location, navigation, and to calibrate other sensors, when appropriate, such as for determining distance between two time points in clear sky conditions and using the distance data to calibrate other sensors such as the odometer and/or LIDAR. In an embodiment, GNSS-based relative locations, based on, for example shared Doppler and/or pseudo-range measurements between vehicles, may be used to determine highly accurate distances between two vehicles, and when combined with vehicle information such as shape and model information and GNSS antenna location, may be used to calibrate, validate and/or affect the confidence level associated with information from LIDAR, camera, RADAR, SONAR and other distance estimation techniques. GNSS Doppler measurements may also be utilized to determine linear motion and rotational motion of the vehicle or of the vehicle relative to another vehicle, which may be utilized in conjunction with gyro and/or magnetometer and other sensor systems to maintain calibration of those systems based upon measured location data. Relative GNSS positional data may also be combined with high confidence absolute locations from road-side units (RSUs), to determine high confidence absolute locations of the vehicle. Furthermore, relative GNSS positional data may be used during inclement weather that may obscure LIDAR and/or camera-based data sources to avoid other vehicles and to stay in the lane or other allocated road area. For example, using a road-side unit (RSU) equipped with GNSS receiver and V2X capability, GNSS measurement data may be provided to the vehicle, which, if provided with an absolute location of the RSU, may be used to navigate the vehicle relative to a map, keeping the vehicle in lane and/or on the road, in spite of lack of visibility.

RADAR 1020, uses transmitted radio waves that are reflected off of objects. The reflected radio waves are analyzed, based on the time taken for reflections to arrive and other signal characteristics of the reflected waves to determine the location of nearby objects. RADAR 1020 may be utilized to detect the location of nearby cars, roadside objects (signs, other vehicles, pedestrians, etc.) and will generally enable detection of objects even if there is obscuring weather such as snow, rail or hail. Thus, RADAR 1020 may be used to complement LIDAR 1014 and camera(s) 1012 in providing ranging information to other objects by providing ranging and distance measurements and information when visual-based systems typically fail. Furthermore, RADAR 1020 may be utilized to calibrate and/or sanity check other systems such as LIDAR 1014 and camera(s) 1012. Ranging measurements from RADAR 1020 may be utilized to determine/measure stopping distance at current speed, acceleration, maneuverability at current speed and/or turning radius at current speed and/or a measure of maneuverability at current speed. In some systems, ground penetrating RADAR may also be used to track road surfaces via, for example, RADAR-reflective markers on the road surface or terrain features such as ditches.

Physiological sensor(s) 1028 may include one or more sensors configured to measure electrodermal activity (EDA). EDA is the property of the human body that causes continuous variation in the electrical characteristics of the skin. Any suitable combination of physiological sensor(s) 1028 may be configured to measure skin conductance, galvanic skin response (GSR), electrodermal response (EDR), psychogalvanic reflex (PGR), skin conductance response (SCR), sympathetic skin response (SSR), skin conductance level (SCL) and the like. By way of example, physiological sensor(s) 1028 may include one or more: galvanic skin response sensors configured to measure GSR, skin conductance sensors configured to measure skin conductance, EDR sensors configured to measure electrodermal responses, PGR sensors configured to measure psychogalvanic reflexes, SCR sensors configured to measure skin conductance responses, SSR sensors configured to measure sympathetic skin responses, SCL sensors configured to measure skin conductance levels (e.g., localized sweating), and the like. In some embodiments, a single physiological sensor can measure both the SCL and the SCR.

In some embodiments, physiological sensor(s) 1028 may include one or more sensors configured to obtain (e.g., capture, measure, calculate) heart rate (HR) and/or heartrate variability (HRV) parameters. Heart rate variability consists of changes in the time intervals between consecutive heartbeats called interbeat intervals (IBIs). A healthy heart is not a metronome. The oscillations of a healthy heart are complex and constantly changing, which allow the cardiovascular system to rapidly adjust to sudden physical and psychological challenges to homeostasis. HRV parameters may include the Root Mean Square of the Successive Differences (RMSSD) between successive heart beats. The Task Force of the European Society of Cardiology and the North American Society of Pacing and Electrophysiology divided heart rate (HR) oscillations into ultra-low-frequency (ULF), very-low-frequency (VLF), low-frequency (LF), and high-frequency (HF) bands. In some embodiments, HRV parameters provided by the physiological sensor(s) 1028 may include heart rate oscillations parameters such as any suitable combination of the ULF, VLF, LF, HF, LF/HF (referred to as the ratio of LF-to-HF power), or any suitable ratio of the above heart rate oscillations parameters. The physiological sensor(s) 1028 may include heart rate monitors (HRMs), electrocardiography (ECG) sensors (also called EKG sensors) configured to measure electrical heart information, photoplethysmography (PPG) sensors configured to measure blood volume, and the like. ECG (Electrocardiography) sensors measure the bio-potential generated by electrical signals that control the expansion and contraction of heart chambers, typically implemented in medical devices. PPG sensors use a light-based technology to measure the blood volume controlled by the heart's pumping action. A PPG sensor can be configured to measure pulse transit time (PTT) which is defined as the time the pulse needs to reach two different distal parts of the body. A PPG sensor may be configured to measure blood volume pulse (BVP). The BVP is widely used as a method of measuring the pulse rate. The BVP can be used to infer heart rate based on the volume of blood that passes through the tissues in a localized area with each beat (pulse) of the heart. In some embodiments, BVP amplitude may be measured. BVP amplitude may be a measure of vasoconstriction/vasodilation—tied to the sympathetic (stress response) and to the thermoregulatory (sick) response.

The physiological sensor(s) 1028, in some embodiments, may include one or more respiration sensors configured to measure breathes per minute and/or breath volume, one or more thermometers configured to measure body temperature (e.g., at a localized part of the body) and/or ambient temperature, or the like.

In some embodiments, memory 1004 may store instructions that, when executed by the processor(s) 1002 implement the motion sickness detection engine 1030. The motion sickness detection engine 830 may store code for performing any suitable combination of the methods, calculations, and/or operations discussed above in connection with FIGS. 1-9.

FIG. 11 is a perspective view of an example vehicle 1100 (e.g., an example of the vehicle 1000 of FIG. 10), according to an embodiment. Here, some of the components discussed with regard to FIG. 11 and earlier embodiments are shown. As illustrated and previously discussed, the vehicle 1100 can have camera(s) 1102 (e.g., an example of camera(s) 1012 of FIG. 10) such as a rear view mirror-mounted camera 1104, a passenger facing camera (not shown), front fender-mounted camera (not shown), side mirror-mounted camera (not shown) and a rear camera (not shown, but typically on the trunk, hatch or rear bumper). Vehicle 1100 may also have LIDAR 1106, for detecting objects and measuring distances to those objects; LIDAR 1106 is often roof-mounted, however, if there are multiple LIDAR units, they may be oriented around the front, rear and sides of the vehicle. Vehicle 1100 may have other various location-related systems such as a receiver 1108 such as a GNSS wireless receiver (typically located in the shark fin unit on the rear of the roof, as indicated) and/or various wireless transceivers (such as WAN, WLAN, V2X; typically, but not necessarily, located in the shark fin), RADAR 1110 (typically in the front bumper), and SONAR 1112 (typically located on both sides of the vehicle, if present. Sensors 1114 may also be present and may include wheel sensors and/or drive train sensors such as tire pressure sensors, accelerometers, gyros, and wheel rotation detection and/or counters. In some embodiments, any suitable combination of sensors 1114 may be utilized to determine and/or measure oscillations of the vehicle 1100 and/or one or more portions of the vehicle.

In an embodiment, distance measurements and relative locations determined via various sensors such as LIDAR, RADAR, camera, GNSS, and SONAR, may be combined with automotive size and shape information and information regarding the location of the sensor to determine distances and relative locations between the surfaces of different vehicles, such that a distance or vector from a sensor to another vehicle or between two different sensors (such as two GNSS receivers) is incrementally increased to account for the position of the sensor on each vehicle. Thus, an exact GNSS distance and vector between two GNSS receivers would need to be modified based upon the relative location of the various car surfaces to the GNSS receiver. For example, in determining the distance between a rear car's front bumper and a leading car's rear bumper, the distance would need to be adjusted based on the distance between the GNSS receiver and the front bumper on the following car, and the distance between the GNSS receiver of the front car and the rear bumper of the front car. By way of example, the distance between the front car's rear bumper and the following car's front bumper is the relative distance between the two GNSS receivers minus the GNSS receiver to front bumper distance of the rear car and minus the GNSS receiver to rear bumper distance of the front car. It is realized that this list is not intended to be limiting and that FIG. 11 is intended to provide exemplary locations of various sensors in an embodiment of vehicle 1100.

FIG. 12 is a schematic diagram depicting an example configuration 1200 of a number of camera(s) positioned to collect eye gaze data and a number of physiological sensors positioned to collect and/or measure physiological data corresponding to an occupant (e.g., occupant 1202) of a vehicle (e.g., vehicle 1000 of FIG. 10), according to an embodiment. Configuration 1200 is provided as an example and is not intended to limit this disclosure. Other configurations are contemplated including the same or a different number and/or type of sensors may be utilized to collect and/or measure any suitable physiological data of the occupant 1202.

Configuration 1200 includes camera 1204 (e.g., an example of camera(s) 1012 of FIG. 10). Camera 1204 may be positioned so as to face occupant 1202 in a manner that enables the camera 1204 to capture eye gaze data (e.g., one or more images/video) of the occupant 1202 over time. In some embodiments, the camera 1204 may be positioned so as to eye gaze data of the occupant's face and/or eyes. These images/video may be processed (e.g., by the processor(s) 1002 of FIG. 10) and any suitable image recognition and/or eye tracking techniques may be utilized to identify the gaze of the occupant 1202 (e.g., a direction toward which the occupant 1202 is looking, an amount by which the user's gaze deviates from the horizon, whether the occupant 1202 is looking toward the horizon or not, whether the occupant is looking out a window or not, etc.).

Configuration 1200 may include any suitable combination of the physiological sensor(s) 1028 of FIG. 10. As depicted in FIG. 12, the physiological sensor(s) 1028 include two galvanic skin response (GSR) sensors (e.g., GSR sensor 1006 and GSR sensor 1008) although a greater or lesser number of GSR sensors may be utilized. FIG. 12 depicts GSR sensor 1206 as being placed at the forehead of occupant 1202. In some embodiments, GSR sensor 1206 may be a component of another device or object such as a headband, sunglasses, or the like (not depicted). GSR sensor 1206 may be positioned to measure galvanic skin responses at the forehead. FIG. 12 depicts GSR sensor 1008 as being positioned to measure the galvanic skin responses at the fingers of the occupant 1202. In some embodiments, GSR sensor 1208 may be incorporated into the steering wheel of a car, a wearable device (e.g., a smartwatch), or the like. Although GSR sensors 1206 and 1208 are depicted, any suitable number of sensors may be similarly utilized at any suitable location of the body to measure skin conductance, galvanic skin response (GSR), electrodermal response (EDR), psychogalvanic reflex (PGR), skin conductance response (SCR), sympathetic skin response (SSR, skin conductance level (SCL) (e.g., sweating), and the like FIG. 12 depicts skin temperature sensor 1209 configured to measure skin temperature at the fingers of the occupant 1202. In some embodiments, skin temperature sensor 1209 may be incorporated into the steering wheel of a car, a wearable device (e.g., a smartwatch), or the like. Although only one skin temperature sensor is depicted, any suitable number of temperature sensors may be similarly utilized at any suitable location of the body.

In some embodiments, physiological sensor(s) 1028 may include one or more sensors configured to obtain (e.g., capture, measure, calculate) heart rate (HR) and/or heartrate variability (HRV) parameters. As depicted in FIG. 12, a electrocardiography (ECG) sensor 1210 is positioned so as to measure heart rate (HR) and heart rate variability (HRV) of the occupant 1202. HRV parameters may include the Root Mean Square of the Successive Differences (RMSSD) between successive heart beats. In some embodiments, the HRV parameters may include an ultra-low-frequency (ULF) band, very-low-frequency (VLF) band, low-frequency (LF) band, and high-frequency (HF) bands band, or any suitable combination and/or ratio of the above. In some embodiments, ECG sensor 1210 measures an electrical signal and standard electrodes by directly contacting the skin. However, in some embodiments, a capacitive heart rate sensor may be utilized through the material of a car seat.

As depicted in FIG. 12, the occupant 1202 may utilize a wearable device (e.g., a watch, a ring, glasses at the temple, etc.) configured with a photoplethysmography (PPG) sensor (e.g., PPG sensor 1212). PPG sensor 1212 may be configured to measure blood volume, and the like. PPG sensor 1212 may measure a pulse transit time (PTT) and/or blood volume pulse (BVP) of the occupant 1202 (and/or other occupants of the vehicle). In some embodiments, BVP can be measured with a camera using image processing algorithms configured to identify BVP from images. Any suitable number of the physiological sensor(s) 1028 may be utilized and may be configured to communicate with one another and/or the processor(s) 1002 of FIG. 10 via any suitable wireless communications protocol. Other combinations and configurations of the physiological sensor(s) 1028 are contemplated.

As depicted in FIG. 12, an IMU 1214 (e.g., including any suitable number of vehicle sensor(s) 1010 of FIG. 10) may be located in the vehicle occupied by the occupant 1202. IMU 1214 may be utilized to measure motion of the vehicle. The IMU 1214 may include any suitable number of accelerometers, gyroscopes, and/or magnetometers configured to measure amplitude and frequency of oscillations of the vehicle and/or parts of the vehicle in which occupant 1202 is located. Thus, in some embodiments, the IMU 1214 is utilized to capture vehicle motion data described above in connection with FIGS. 1, 4, and 5.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

With reference to the appended figures, components that can include memory (e.g., memory 1004 of FIG. 10) can include non-transitory machine-readable media. The term "machine-readable medium" and "computer-readable medium" as used herein, refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media, any other physical medium with patterns of holes, a RAM, a PROM, EPROM, a FLASH-EPROM, any other memory chip or cartridge, a carrier wave as described hereinafter, or any other medium from which a computer can read instructions and/or code.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this Specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this Specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several embodiments, various modifications, alternative constructions, and equivalents may be used without departing from the spirit of the disclosure. For example, the above elements may merely be a component of a larger system, wherein other rules may take precedence over or otherwise modify the application of the various embodiments. Also, a number of steps may be undertaken before, during, or after the above elements are considered. Accordingly, the above description does not limit the scope of the disclosure.

What is claimed is:

1. A method for preventing or ameliorating motion sickness of a user within a vehicle, comprising:
    obtaining, by one or more processors from a plurality of sensor devices, a first set of physiological data related to the user within the vehicle;
    obtaining, by the one or more processors from the plurality of sensor devices, a second set of physiological data related to the user, wherein the second set of physiological data is captured by the plurality of sensor devices after the first set of physiological data is captured by the plurality of sensor devices;
    obtaining, by the one or more processors from the plurality of sensor devices, a third set of physiological data related to the user, wherein the third set of physiological data is captured by the plurality of sensor devices after the first set of physiological data and the second set of physiological data are captured by the plurality of sensor devices;
    determining a first set of physiological features of the user from the first set of physiological data;
    determining a second set of physiological features of the user from the second set of physiological data;
    determining a third set of physiological features of the user from the third set of physiological data;
    determining that the user has experienced a stress response based at least in part on comparing the second set of physiological features to the first set of physiological features;
    subsequent to determining that the user has experienced the stress response, determining that the user has experienced a sick response after experiencing the stress response based at least in part on comparing the third set of physiological features to the second set of physiological features;
    obtaining, by the one or more processors, vehicle motion data of the vehicle;
    calculating, by the one or more processors, a motion sickness score based at least in part on determining the user has experienced the sick response after experiencing the stress response and the vehicle motion data;
    detecting, by the one or more processors, that the user is experiencing a degree of motion sickness based at least in part on the motion sickness score; and
    performing, by the one or more processors, an autonomous vehicle action in response to determining that the user is experiencing the degree of motion sickness, wherein performing the autonomous vehicle action ameliorates the degree of motion sickness experienced by the user at a subsequent time or prevents an escalation in the degree of motion sickness experienced by the user at the subsequent time.

2. The method of claim 1, further comprising:
    obtaining, by the one or more processors from an image capture device, eye gaze data, the eye gaze data comprising one or more images indicating a gaze of the user, wherein the motion sickness score is calculated further based at least in part on the one or more images indicating the gaze of the user.

3. The method of claim 1, wherein the vehicle motion data comprises one or more oscillation measurements, and wherein the method further comprises determining that a frequency of the oscillation measurements falls within a predefined range.

4. The method of claim 1, wherein the autonomous vehicle action comprises: slowing the vehicle down, modifying a route, performing less aggressive turns, maintaining a more constant heading, or any combination of the above.

5. The method of claim 1, wherein the plurality of sensor devices comprises a first sensor and a second sensor each configured to measure galvanic skin responses of the user and a third sensor configured to measure heart rate of the user.

6. The method of claim 5, wherein the first sensor is positioned to measure a first galvanic skin response at a forehead of the user, and wherein the second sensor is positioned to measure a second galvanic skin response at a palmer surface or wrist of the user.

7. The method of claim 1, wherein the first set of physiological features comprises:
    a heart rate of the user,
    an average skin temperature, one or more skin conductance levels corresponding to one or more areas of skin of the user, one or more skin conductance responses corresponding to the one or more areas of skin of the user, a root mean square of successive differences between normal heartbeats of the user, and a blood volume pulse amplitude indicating relative blood flow, or any combination of the above.

8. The method of claim 7, further comprising obtaining a set of baseline physiological features associated with the user, and wherein determining the user has experienced the stress response is based at least in part on comparing the first set of physiological features to the set of baseline physiological features.

9. The method of claim 1, wherein the detecting, by the one or more processors, that the user is experiencing the degree of motion sickness based at least in part on the motion sickness score comprises:

determining, using a first machine learning model, based on the first set of physiological features of the user, that the user has experienced the stress response; and determining, using a second machine learning model, based on the second set of physiological features of the user, that the user has experienced the sick response.

10. The method of claim 9, wherein:

the first machine learning model comprises a first classification model trained using supervised learning, a first training data set to classify input data, and at least a first classification value corresponding to the stress response, and the second machine learning model comprises a second classification model trained using supervised learning, a second training data set to classify input data, and at least a second classification value corresponding to the sick response.

11. A computing device, comprising:

a memory storing executable instructions for preventing or ameliorating a degree of motion sickness experienced by a user within a vehicle; and one or more processors communicatively coupled with the memory, the one or more processors being configured to execute the instructions to cause the computing device to:

obtain a first set of physiological data from a plurality of sensor devices;

obtain a second set of physiological data from the plurality of sensor devices, wherein the second set of physiological data is captured by the plurality of sensor devices after the first set of physiological data is captured by the plurality of sensor device;

obtain, by the one or more processors from the plurality of sensor devices, a third set of physiological data related to the user, wherein the third set of physiological data is captured by the plurality of sensor devices after the first set of physiological data and the second set of physiological data are captured by the plurality of sensor devices;

determine a first set of physiological features of the user from the first set of physiological data;

determine a second set of physiological features of the user from the second set of physiological data;

determine a third set of physiological features of the user from the third set of physiological data;

determine that the user has experienced a stress response based at least in part on comparing the second set of physiological features to the first set of physiological features;

subsequent to determining that the user has experienced the stress response, determine that the user has experienced a sick response after experiencing the stress response based at least in part on comparing the third set of physiological features to the second set of physiological features;

obtain vehicle motion data indicating a frequency of oscillations of the vehicle;

calculate a motion sickness score based at least in part on the determining the user has experienced the sick response after experiencing the stress response and the vehicle motion data;

detect that the user is experiencing a degree of motion sickness based at least in part on the motion sickness score; and cause performance of an autonomous vehicle action in response to determining that the user is experiencing the degree of motion sickness, wherein causing the autonomous vehicle action to be performed ameliorates the degree of motion sickness experienced by the user or prevents an escalation in the degree of motion sickness experienced by the user at the subsequent time.

12. The computing device of claim 11, wherein executing the instructions further causes the computing device to:

obtain, from an image capture device, eye gaze data, the eye gaze data comprising one or more images indicating a gaze of the user, wherein the motion sickness score is calculated further based at least in part on the one or more images indicating the gaze of the user.

13. The computing device of claim 11, wherein the vehicle motion data comprises one or more oscillation measurements, and wherein executing the instructions further causes the computing device to determine that a frequency of the oscillation measurements falls within a predefined range.

14. The computing device of claim 11, wherein the autonomous vehicle action comprises: slowing the vehicle down, modifying a route, performing less aggressive turns, maintaining a more constant heading, or any combination of the above.

15. The computing device of claim 11, wherein the plurality of sensor devices comprises a first sensor and a second sensor each configured to measure galvanic skin responses of the user and a third sensor configured to measure heart rate of the user.

16. The computing device of claim 15, wherein the first sensor is positioned to measure a first galvanic skin response at a forehead of the user, and wherein the second sensor is positioned to measure a second galvanic skin response at a palmer surface or wrist of the user.

17. The computing device of claim 16, wherein the first set of physiological features comprises:

a heart rate of the user, an average skin temperature, one or more skin conductance levels corresponding to one or more areas of skin of the user, one or more skin conductance responses corresponding to the one or more areas of skin of the user, a root mean square of successive differences between normal heartbeats of the user, and a blood volume pulse amplitude indicating relative blood flow, or any combination of the above.

18. The computing device of claim 17, wherein executing the instructions further causes the computing device to:
obtain a set of baseline physiological features associated with the user; and
determine the user has experienced the stress response based at least in part on comparing the first set of physiological features to the set of baseline physiological features.

19. The computing device of claim 11, wherein the detecting, by the one or more processors, that the user is experiencing the degree of motion sickness based at least in part on the motion sickness score comprises:
determining, using a first machine learning model, based on the first set of physiological features of the user, that the user has experienced the stress response; and
determining, using a second machine learning model, based on the second set of physiological features of the user, that the user has experienced the sick response.

20. The computing device of claim 19, wherein:
the first machine learning model comprises a first classification model trained using supervised learning, a first training data set to classify input data, and at least a first classification value corresponding to the stress response, and
the second machine learning model comprises a second classification model trained using supervised learning, a second training data set to classify input data, and at least a second classification value corresponding to the sick response.

21. A non-transitory computer-readable medium having instructions stored for preventing or ameliorating a degree of motion sickness experienced by a user within a vehicle, wherein the instructions, when executed by one or more processing units, cause the one or more processing units to:
obtain a first set of physiological data from a plurality of sensor devices;
obtain a second set of physiological data from the plurality of sensor devices, wherein the second set of physiological data is captured by the plurality of sensor devices after the first set of physiological data is captured by the plurality of sensor device;
obtain a third set of physiological data related to the user, wherein the third set of physiological data is captured by the plurality of sensor devices after the first set of physiological data and the second set of physiological data are captured by the plurality of sensor devices;
determine a first set of physiological features of the user from the first set of physiological data;
determine a second set of physiological features of the user from the second set of physiological data;
determine a third set of physiological features of the user from the third set of physiological data;
determine that the user has experienced a stress response based at least in part on comparing the second set of physiological features to the first set of physiological features;
subsequent to determining that the user has experienced the stress response, determine that the user has experienced a sick response after experiencing the stress response based at least in part on comparing the third set of physiological features to the second set of physiological features;
obtain vehicle motion data indicating a frequency of oscillations of the vehicle;
calculate a motion sickness score based at least in part on the determining the user has experienced the sick response after experiencing the stress response and the vehicle motion data;
detect that the user is experiencing a degree of motion sickness based at least in part on the motion sickness score; and
cause performance of an autonomous vehicle action in response to determining that the user is experiencing the degree of motion sickness, wherein causing the autonomous vehicle action to be performed ameliorates the degree of motion sickness experienced by the user or prevents an escalation in the degree of motion sickness experienced by the user at the subsequent time.

22. The non-transitory computer-readable medium of claim 21, wherein the instructions, when executed by the one or more processing units, further cause the one or more processing units to obtain, from an image capture device, eye gaze data, the eye gaze data comprising one or more images indicating a gaze of the user, wherein the motion sickness score is calculated further based at least in part on the one or more images indicating the gaze of the user.

23. The non-transitory computer-readable medium of claim 21, wherein the vehicle motion data comprises one or more oscillation measurements, and wherein the instructions, when executed by the one or more processing units, further cause the one or more processing units to determine that a frequency of the oscillation measurements falls within a predefined range.

24. The non-transitory computer-readable medium of claim 21, wherein the autonomous vehicle action comprises: slowing the vehicle down, modifying a route, performing less aggressive turns, maintaining a more constant heading, or any combination of the above.

25. The non-transitory computer-readable medium of claim 21, wherein the instructions, when executed by the one or more processing units, further cause the one or more processing units to:
obtain a set of baseline physiological features associated with the user; and
determine the user has experienced the stress response based at least in part on comparing the first set of physiological features to the set of baseline physiological features.

26. The non-transitory computer-readable medium of claim 21, wherein the detecting, by the one or more processors, that the user is experiencing the degree of motion sickness based at least in part on the motion sickness score comprises:
determining, using a first machine learning model, based on the first set of physiological features of the user, that the user has experienced the stress response; and
determining, using a second machine learning model, based on the second set of physiological features of the user, that the user has experienced the sick response.

27. The non-transitory computer-readable medium of claim 26, wherein:
the first machine learning model comprises a first classification model trained using supervised learning, a first training data set to classify input data, and at least a first classification value corresponding to the stress response, and
the second machine learning model comprises a second classification model trained using supervised learning, a second training data set to classify input data, and at least a second classification value corresponding to the sick response.

\* \* \* \* \*